US012653956B2

(12) United States Patent
Livingston et al.

(10) Patent No.: US 12,653,956 B2
(45) Date of Patent: Jun. 16, 2026

(54) LIQUID DELIVERY CAP WITH ALIGNMENT VERIFICATION

(71) Applicant: PATIENTS PENDING LTD., London (GB)

(72) Inventors: Adam Joseph Livingston, Oceanside, CA (US); George Crothall, Oceanside, CA (US); Jeffrey Michael Johnson, San Diego, CA (US)

(73) Assignee: PATIENTS PENDING LTD., London (GB)

( * ) Notice: Subject to any disclaimer, the term of this patent is extended or adjusted under 35 U.S.C. 154(b) by 1213 days.

(21) Appl. No.: 17/596,853

(22) PCT Filed: Jun. 19, 2020

(86) PCT No.: PCT/IB2020/055813
§ 371 (c)(1),
(2) Date: Dec. 20, 2021

(87) PCT Pub. No.: WO2020/255085
PCT Pub. Date: Dec. 24, 2020

(65) Prior Publication Data
US 2022/0305210 A1       Sep. 29, 2022

Related U.S. Application Data

(60) Provisional application No. 62/864,247, filed on Jun. 20, 2019.

(51) Int. Cl.
*A61M 5/315*        (2006.01)
*A61M 5/32*         (2006.01)

(52) U.S. Cl.
CPC ...... *A61M 5/31568* (2013.01); *A61M 5/3202* (2013.01); *A61M 2205/3306* (2013.01); *A61M 2205/3327* (2013.01)

(58) Field of Classification Search
CPC ............ A61M 5/31568; A61M 5/3202; A61M 5/3157; A61M 2205/3306;
(Continued)

(56) References Cited

U.S. PATENT DOCUMENTS 8,743,662 B2     6/2014  Sjolund et al.
2015/0144793 A1*  5/2015  Whalley ........... A61M 5/16886
                                                    250/357.1
(Continued)

FOREIGN PATENT DOCUMENTS

CN        106456885 A      2/2017
CN        106537095 A      3/2017
(Continued)

OTHER PUBLICATIONS

International Search Report and Written Opinion of PCT/IB2020/055813, Sep. 14, 2020, 11 pages.
(Continued)

*Primary Examiner* — Michael J Tsai
*Assistant Examiner* — Justin L Zamory
(74) *Attorney, Agent, or Firm* — HSML P.C.

(57) ABSTRACT

A cap device for a liquid delivery device operates to detect a position of the liquid delivery device relative to the cap device as the liquid delivery device is inserted to the cap device and rotated relative to the cap device. The cap device includes one or more sensors configured to detect a position of the liquid delivery device relative to the cap device. The position of the liquid delivery device can be used to determine whether the liquid delivery device is inserted and arranged in an appropriate axial and/or radial position relative to the cap device so that the cap device can accurately detect a condition of the liquid delivery device.

19 Claims, 12 Drawing Sheets

(58) Field of Classification Search
CPC ....... A61M 2205/3327; A61M 2205/581–583;
A61M 2039/1044
See application file for complete search history.

(56) References Cited

U.S. PATENT DOCUMENTS

| 2016/0051760 | A1 | 2/2016 | Krusell et al. |
| 2016/0259913 | A1 | 9/2016 | Yu et al. |
| 2017/0112369 | A1* | 4/2017 | Czupalla ............ A61B 1/00193 |
| 2018/0200451 | A1 | 7/2018 | Shekalim |

FOREIGN PATENT DOCUMENTS

| CN | 107431301 | A | 12/2017 |
| CN | 107456620 | A | 12/2017 |
| CN | 108139313 | A | 6/2018 |
| CN | 108348693 | A | 7/2018 |
| CN | 108601897 | A | 9/2018 |
| CN | 108697855 | A | 10/2018 |
| EP | 0 688 572 | | 12/1995 |
| EP | 1095668 | A1 | 5/2001 |
| EP | 2879740 | B1 | 3/2017 |
| WO | 02/092153 | | 11/2002 |
| WO | 2004/010231 | | 1/2004 |
| WO | 2014/128156 | A1 | 8/2014 |

OTHER PUBLICATIONS

Office Action and search report issued for Chinese Patent Application No. 202080056655.4, Apr. 3, 2024, 23 pages including machine translation of the Office Action.

* cited by examiner

3hr 10min
since last dose

LIQUID DELIVERY CAP WITH ALIGNMENT VERIFICATION

TECHNICAL FIELD

This document describes devices, systems, and methods related to cap devices of a liquid delivery device, for example, cap devices configured to detect a plunger of the liquid delivery device.

BACKGROUND

Liquid delivery systems are commonly used to deliver a measured quantity of a drug to a patient. For example, pen-injector delivery devices have been used to deliver a measured quantity of a drug, and include a delivery end that is capped for storage between uses and a plunger movable within a reservoir to dispense a measured dose. A cap device may protect the delivery end from damage during storage and may be used to display information to a user, such as a duration since the cap was last removed during a previous use of the injection device or information about the contents of the delivery device.

SUMMARY

Some embodiments described herein include cap devices, systems, and methods configured to detect a position (e.g., such as a radial orientation or axial position) of a liquid delivery device relative to a cap device, a condition of the liquid delivery device, and/or output dosage information based at least in part on the detected condition. For example, a liquid delivery system may include a liquid delivery device having a reservoir and a movable plunger to force liquid from the reservoir, and a cap device configured to cover at least a delivery end of the liquid delivery device. The cap device includes one or more sensors configured to detect a position of the liquid delivery device relative to the cap device, and/or detect a condition of the liquid delivery device. For example, the position of the liquid delivery device can be used to determine whether the liquid delivery device is inserted and arranged in an appropriate axial and/or radial position relative to the cap device so that the cap device can accurately detect a condition of the liquid delivery device. Alternatively or additionally, detected position information may be used during subsequent determination of a condition of the liquid delivery device. The condition of the liquid delivery device may include a position of the plunger that can be used to determine the liquid volume within the reservoir, dosage information (e.g. the volume of a previously delivered dose), and/or other information related to the liquid delivery device and its operation. In an example embodiment, detection of appropriate axial and/or radial alignment facilitates detection of accurate and robust liquid volume and dosage information.

In some examples, a cap device is configured to axially receive at least a portion of the liquid delivery device in the cap device such that the liquid delivery device is at least partially rotatable relative to the cap device. In some embodiments, the cap device is configured to axially receive a liquid delivery device in multiple possible orientations and provide a feedback, such as mechanical (e.g., clicking/detent sensation), visible, and/or audible feedback, to indicate that the liquid delivery device is inserted to a predetermined axial position. Alternatively or in addition, the cap device is configured to detect that a liquid delivery device is axially inserted in the cap device (e.g., engaged with the cap device)

and/or to detect an axial alignment position of the liquid delivery device relative to the cap device. Further, in some embodiments, the cap device may be configured to detect a radial position of the liquid delivery device and determine whether the liquid delivery device is rotated to a predetermined radial position (e.g., radial alignment position) relative to the cap device (e.g., as a user turns the liquid delivery device relative to the cap device). For example, the cap device monitors a change in sensor signals generated by one or more sensors and detects a predetermined feature of the liquid delivery device based on the change of the sensor signals when the liquid delivery device has been rotated to a predetermined orientation. In addition, the cap device may be configured to provide a feedback, such as a mechanical (e.g., clicking/detent sensation), visible, and/or audible feedback, to make sure that the liquid delivery device is rotated to the predetermined radial position and/or that the liquid delivery device is not rotated past the predetermined radial position. The radial alignment position may be a single radial position or a plurality of radial positions that each provide a suitable line of sight for accurate plunger detection. Similarly, the axial alignment position may include one or more axial positions that allow the liquid delivery device to be rotated to the radial alignment position, and/or one or more axial positions in which the liquid delivery device is engaged with the cap device.

Some example cap devices may include one or more mechanical feedback structures, such as user-perceptible detents, snaps, and other mechanical interactions, that generate physical feedback (e.g., clicking sensation) when the liquid delivery device is engaged with the cap device in the axial direction and/or when the liquid delivery device is in the predetermined radial position.

Some example cap devices may provide one or more outputs related to a relative position of the cap device and the liquid delivery device. For example, the cap device includes one or more output devices that output information indicative of the axial position and/or the radial position of the liquid delivery device with respect to the cap device. Further, the cap device can present information to prompt and/or assist a user to insert and align the liquid delivery device in the cap device. The information can be presented in various forms, such as visible, audible, and/or tactile forms. In some embodiments, the output device includes a display device configured to display symbols (e.g., signs, texts, letters, numbers, colors, animations, etc.) that indicate a position of the liquid delivery device relative to the body, such as whether the liquid delivery device is in the axial alignment position and/or the radial alignment position. Such display of symbols may be used to encourage a user to properly insert and arrange the liquid delivery device in the cap device to facilitate accurate and reliable measurement.

In some embodiments, the cap device optionally includes a body and a sensor carriage movably located within the body. At least one of the sensors configured to detect a radial position of the liquid delivery device relative to the cap device can be mounted on the sensor carriage. Alternatively or additionally, one or more of the sensors configured to detect a radial position of the liquid delivery device relative to the cap device may be fixedly positioned relative to the body of the cap device.

The sensors may operate to output sensor signals. The sensor signals may vary based on features of the liquid delivery device encountered by the one or more sensors. For example, the sensor signals can differ depending on where the liquid delivery device is positioned, axially and/or radially, relative to the cap device. Further, the sensor signals can vary based on a plunger or liquid within the reservoir, transparent or opaque features, numbering/lettering, graduation markings, etc. In some embodiments, the sensor carriage may be movable between first and second positions without user operation, or movable by positioning the cap device on the liquid delivery device without additional user operation.

Some example cap devices may facilitate arrangement of the liquid delivery device with respect to the cap device in axial and/or radial positions that allow accurate and repeatable detection of the plunger position of the liquid delivery device. The plunger position can be used to determine the volume of a previously delivered dose or the volume remaining in the reservoir, for example. Alternatively or additionally, some embodiments facilitate accurate and repeatable measurement by reducing manual manipulation during detection. For example, the sensor carriage may move between first and second positions while the liquid delivery device is at least partially received in the cap device, and without additional manual operation by a user beyond the operation of engaging the liquid delivery device with the cap device.

Some example cap devices may determine that a liquid delivery device is not in radial alignment with a cap device at a first time, and then determine that the liquid delivery device becomes radial alignment with the cap device at a later second time. The radial alignment permits for the cap devices to obtain accurate measurement of a condition of the liquid delivery device (e.g., a plunger position, an amount of liquid remaining in the liquid delivery device, etc.) at the second time, while radial misalignment may cause inaccurate measurement of the condition of the liquid delivery device. By way of example, a user may neglect to put a cap device and a liquid delivery device into a predetermined radial alignment after axially inserting the cap device over the liquid delivery device. If a user subsequently removes the cap device from the liquid delivery device (e.g., for a subsequent injection of liquid) without the cap device and the liquid delivery device previously being in the predetermined radial alignment, and then subsequently replaces the cap device onto the liquid delivery device in the predetermined radial alignment at a later time, the cap can determine an approximated condition of the liquid delivery device (e.g., the plunger position, the amount of liquid remaining in the liquid delivery device, etc.) at both the earlier and later times. The cap device can determine the approximated condition of the liquid delivery device at the earlier time (when the cap device was in radial misalignment) based on, for example, a blood glucose response of a user, a historical dose for the user, a therapy parameter for the user, or any other information that can approximate the conditions.

Particular embodiments described herein include a cap device for a liquid delivery device. The cap device may include a body and a first sensor. The body defines a cavity configured to at least partially receive a liquid delivery device. The first sensor is configured to output a sensor signal indicative of a radial alignment position of the liquid delivery device relative to the body when the liquid delivery device is at least partially received within the cavity of the body.

In some implementations, the cap device can optionally include one or more of the following features.

The cap device may include a second sensor configured to output a sensor signal indicative of a plunger of the liquid delivery device, and a processor configured to determine that the liquid delivery device is not in the radial alignment position at a first time; determine that the liquid delivery device is in the radial alignment position at a second time later than the first time; determine, using the second sensor, a position of the plunger at the second time; and calculate an approximated position of the plunger at the first time based at least in part on the position of the plunger at the second time. The approximated position of the plunger at the first time can be based further on at least one of a blood glucose response of a user, a historical dose for the user, and a therapy parameter for the user.

The cap device may include a processor configured to detect the radial alignment position of the liquid delivery device based on the sensor signal of the first sensor.

The first sensor may be configured to output the sensor signal indicative of a radial alignment position when the first sensor is located at a predetermined axial position along the liquid delivery device.

The cap device may include a sensor carriage movable within the cavity between a first position and a second position while the liquid delivery device is in a fixed position relative to the cavity. The first sensor may be located on the sensor carriage. Alternatively, the first sensor may be fixedly mounted to the body.

The cap device may include a second sensor. The second sensor may be located on the sensor carriage. The second sensor may be configured to output a sensor signal indicative of a plunger of the liquid delivery device while the sensor carriage moves between the first position and the second position.

The cap device may include a motor configured to move the sensor carriage between the first position and the second position.

The processor may be configured to determine a condition associated with the liquid delivery device based on the sensor signal of the first sensor and a sensor signal of the second sensor.

The processor may be configured to record a first time at which the liquid delivery device is axially received in the cavity of the body, and a second time at which the liquid delivery device is moved to the radial alignment position. The processor may determine a condition associated with the liquid delivery device based on the sensor signal of the first sensor, a sensor signal of the second sensor, the first time, and the second time.

The first sensor may include a first optical emitter and a first optical receiver. An optical path may be defined between the first optical emitter and the first optical receiver. The first sensor may operate to detect a physical feature by outputting a sensor signal indicative of the physical feature of the liquid delivery device.

The second sensor may include a second optical emitter and a second optical receiver. An optical path may be defined between the second optical emitter and the second optical receiver. The second sensor may operate to detect a physical feature by outputting a sensor signal indicative of the physical feature of the liquid delivery device.

The cap device may include a position sensor configured to detect an axial position of the sensor carriage within the body. The physical feature of the liquid delivery device may include a plunger of the liquid delivery device. The processor may operate to detect the plunger of the liquid delivery device based on a variation in the sensor signal and to determine a corresponding position of the plunger based on a sensor signal output by the position sensor.

The condition associated with the liquid delivery device may include at least one of a volume of a dose delivered by the liquid delivery device, a remaining total volume of liquid within the liquid delivery device, a remaining number of doses within the liquid delivery device, a remaining duration until the liquid delivery device is emptied, and a time of a previous dose, an elapsed time since a last dose.

The cap device may include an axial position device configured to engage the liquid delivery device that is axially inserted to the cavity of the body. The axial position device may generate a first mechanical feedback upon engagement of the liquid delivery device with the axial position device.

The axial position device may include a sensor configured to generate a sensor signal indicative of the engagement of the liquid delivery device with the axial position device.

The body of the cap device may be configured to axially receive at least a portion of the liquid delivery device in the cavity. The liquid delivery device may be at least partially rotatable relative to the body while the at least a portion of the liquid delivery device is within the cavity.

The sensor carriage may mount the first sensor. The motor may operate to move the sensor carriage to a predetermined axial position in which the first sensor is arranged to detect the radial alignment position of the liquid delivery device.

The cap device may include a radial retention structure configured to generate a second mechanical feedback upon detecting the radial alignment position of the liquid delivery device.

The cap device may include a display device configured to output information indicative of a position of the liquid delivery device relative to the body.

The cap device may include a sleeve configured to receive at least a portion of the liquid delivery device. The sensor carriage may be configured to move along an outside of the sleeve.

Particular embodiments described herein include a method for operating a cap device for a liquid delivery device. The method may include detecting a radial position of a liquid delivery device relative to a body of a cap device while the liquid delivery device is at least partially within the cap device, and outputting information related to the radial position of the liquid delivery device.

In some implementations, the method can optionally include one or more of the following features.

The method may include, prior to detecting the radial position, detecting engagement of the liquid delivery device with the cap device. The liquid delivery device may be rotatable relative to the body of the cap device.

The information may indicate whether the radial position of the liquid delivery device is moved into a predetermined radial alignment position.

The method may further include determining that the liquid delivery device is not in radial alignment with the body of the cap device at a first time; determining that the liquid delivery device is in radial alignment with the body of the cap device at a second time later than the first time; determining a position of the plunger at the second time; and calculating an approximated position of the plunger at the first time based at least in part on the position of the plunger at the second time. The approximated position of the plunger at the first time can be based further on at least one of a blood glucose response of a user, a historical dose for the user, and a therapy parameter for the user.

The method may include generating a first mechanical feedback when the liquid delivery device is moved into a predetermined axial alignment position.

The method may include generating a second mechanical feedback when the radial position of the liquid delivery device is moved into the predetermined radial alignment position.

The method may include activating the cap device when the liquid delivery device is moved into a predetermined axial alignment position.

The method may include detecting a first time at which the liquid delivery device is axially engaged in a cavity of the body, detecting a second time at which the liquid delivery device is in the predetermined radial alignment position, detecting, using a sensor, a feature associated with the liquid delivery device, and determining a condition associated with the liquid delivery device based on the feature, the first time, and the second time.

The detection of a radial position of a liquid delivery device may include receiving, from a first sensor, a sensor signal indicative of a radial alignment position of the liquid delivery device relative to the body of the cap device.

The method may include driving a sensor carriage including the first sensor to a predetermined axial location within the cap device. When the sensor carriage is arranged at the predetermined axial location, the first sensor may be configured to generate the sensor signal indicative of the radial alignment position.

The method may include, upon detecting the radial position of the liquid delivery device, driving a sensor carriage including a second sensor between a first position and a second position within the body of the cap device. The method may further include detecting a physical feature of the liquid delivery device while the sensor carriage moves between the first position and the second position.

The detection of a physical feature of the liquid delivery device may include receiving, from the second sensor, a sensor signal indicative of a sensor signal indicative of a plunger of the liquid delivery device while the sensor carriage moves between the first position and the second position.

Particular embodiments described herein include a cap device. The cap device may include a body and a sensor. The body may be configured to at least partially receive a liquid delivery device. The sensor may be configured to output a sensor signal indicative of a radial position of the liquid delivery device relative to the body.

Particular embodiments described herein include a cap device. The cap device may include a means for at least partially receiving a liquid delivery device, and a means for detecting a radial position of the liquid delivery device.

The devices, system, and techniques described herein may provide one or more of the following advantages. First, some embodiments described herein include a cap device that can facilitate arrangement of a liquid delivery device in a position relative to the cap device that facilitates accurate, reliable, and repeatable measurements related to the liquid delivery device. For example, the cap device includes one or more sensor that detect axial and/or radial positions of a liquid delivery device with respect to the cap device and determine whether the liquid delivery device is in predetermined axial and/or radial alignment relative to the cap device that facilitate accurate, reliable, and repeatable monitoring and determination of a condition associated with the liquid delivery device, such as the liquid volume within the reservoir, dosage information (e.g. the volume of a previously delivered dose, and an amount of medication remaining in the liquid delivery device), and/or other information related to the liquid delivery device and its operation.

Second, some embodiments described herein include a cap device that can assist a user in appropriately positioning the cap device on the liquid delivery device. For example, the cap device may generate feedback to a user to promote axial and/or radial alignment of the liquid delivery device with respect to the cap device. Such feedback may include output of information indicative of a current position of the liquid delivery system, and/or output of information indicative of one or more actions required to arrange the liquid delivery system in predetermined alignment with the cap device (e.g., relative rotation of the cap device and liquid delivery device). The feedback can be provided in different forms, such as audible feedback, tactile, or other visible or physical feedback. In various example embodiments, the output may be generated by the cap device based on one or more sensor signals. Alternatively or additionally, the output may include a user-perceptible detent, snap, mechanical interaction, etc. indicative of appropriate axial alignment, radial alignment, etc.

Third, some embodiments described herein include a cap device that can perform one or more tasks based on a radial alignment of the liquid delivery device relative to the cap device. For example, the cap device may detect a plunger position or other condition of the liquid delivery device based at least in part on information related to a radial position of the liquid delivery device. The plunger position or other condition of the liquid delivery device may be detected after the liquid delivery device is in a predetermined radial alignment. Alternatively or additionally, information about the radial alignment of the liquid deliver device may be used in determining a condition of the liquid delivery device.

Fourth, some embodiments described herein may facilitate dosage detection at a time non-contemporaneous with dose delivery. For example, the cap device may be configured to detect a plunger position or other condition of the liquid delivery device at a time when the liquid delivery device is in an appropriate radial alignment relative to the cap device, which may occur a period of time after dosage and/or initial capping of the liquid delivery device. In other words, detection may occur independent of the time of the dosage.

Fifth, some embodiments described herein may track a change in a condition of the liquid delivery device over time, and, if appropriate, update dosage information related to dosages delivered at a previous time. For example, the cap device may operate to measure/calculate a dose of liquid from the liquid delivery device (e.g., irrespective of whether the liquid delivery device is in a particular predetermined alignment with the cap device, such as when the liquid delivery device is only axially inserted into the cap device and not rotated to a predetermined radial position relative to the cap device). The cap device can operate to identify a time that the liquid delivery device is moved into a predetermined alignment with the cap device, and further operate to measure/calculate a dose of liquid delivered from the liquid delivery device at the earlier time. Such features can facilitate tracking and output of accurate information associated with the liquid delivery device over a period of time.

Sixth, some embodiments described herein include a sensor carriage carrying a sensor component (and/or that is movable with limited or no manual user operation) that can promote a consistent travel velocity and/or acceleration that facilitates consistent and predictable sensor signals. User influence on the dynamics of the sensor carriage may be reduced, and manufacturing design tolerances that may result in clearance play or other inadvertent movement of the sensor carriage during operation of the sensor carriage can be reduced.

Seventh, some embodiments described herein may facilitate accurate and repeatable measurements related to the liquid delivery device by using a combination of sensor types. In some embodiments, the cap device includes one or more optical sensors together with a position sensor, such as a linear potentiometer, optical encoder, rotary encoder, magnetic potentiometer, membrane potentiometer, load cell, etc., for example. The combination of such sensor types facilitates accurate evaluation of relative positions of various features of the liquid delivery device and/or a change in position of various features during subsequent scans of the liquid delivery device.

Eighth, the cap device may promote efficient and cost-effective manufacturing and assembly processes by including relatively few sensors. In some embodiments, the cap device includes one or two liquid delivery device sensors (e.g. plunger sensors), such as one or two optical sensors, and a position sensor, such as a linear potentiometer, optical encoder, rotary encoder, magnetic potentiometer, membrane potentiometer, etc. Such configurations thus include relatively few sensors, and reduce the number of assembly and/or calibration steps that otherwise may be appropriate to assemble many sensors into the cap device.

Ninth, various embodiments described herein may include a cap device compatible with a variety of liquid delivery device types. For example, the cap device may facilitate accurate and repeatable measurements even when used with distinct liquid delivery device types that may have varying shapes, sizes, and features that interact differently with the sensors and other features of the cap device. One or more optical sensors of the sensor carriage may be oriented to obtain predetermined lines of sight that promote reliable plunger detection for a variety of different liquid delivery device types. For example, optical sensors may be arranged so that at least one optical sensor is positioned to detect the plunger, even if another optical sensor is obstructed by a feature of the liquid delivery device at a particular instance.

Tenth, some cap devices described herein improve the user experience of a liquid delivery system by automating some actions related to dose measurement and management. For example, the cap device may deliver output that informs a user of a previously delivered dose of the liquid, a duration since the previous dose, a number of doses remaining, a volume of liquid remaining, an expected life remaining of the liquid delivery device.

Eleventh, in some optional embodiments, cap devices described herein may improve the user experience of a liquid delivery system by facilitating semi-automatic or automatic operation. For example, little or no manual operation may be required beyond engaging the cap device with the liquid delivery device. In some optional embodiments including a movable sensor carriage, the sensor carriage may be brought into a first position by engagement of the cap device onto the liquid delivery device, and the sensor carriage may be automatically released such that the sensor carriage can move from the first position to the second position while operating to scan the liquid delivery device.

Twelfth, some embodiments described herein facilitate a durable cap device that can operate over an extended period of time and/or that may be used with many liquid delivery devices. For example, a single cap device may be reusable with many disposable liquid delivery devices. The sensors of the cap device, such as one or more alignment sensors, one or more plunger sensors and position sensors, such as one or more optical sensors, load sensors, linear potentiometers, optical encoders, rotary encoders, magnetic potentiometers, membrane potentiometers etc., may be configured to have consistent and/or predictable output over the operational life of the cap device.

Thirteenth, some embodiments described herein provide controlled sensor movement that may provide reliable and repeatable detection. For example, a motorized drive system may drive a sensor carriage substantially independent of manual input or movement. In some embodiments, a motorized drive system may drive a sensor carriage at a varied speeds, in multiple directions, etc. to improve detection. Alternatively or additionally, movement of the sensor carriage may be delayed a predetermined period of time after engagement between the cap device and liquid delivery device to facilitate measurement while the system is subject to little or no movement or external forces.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1:
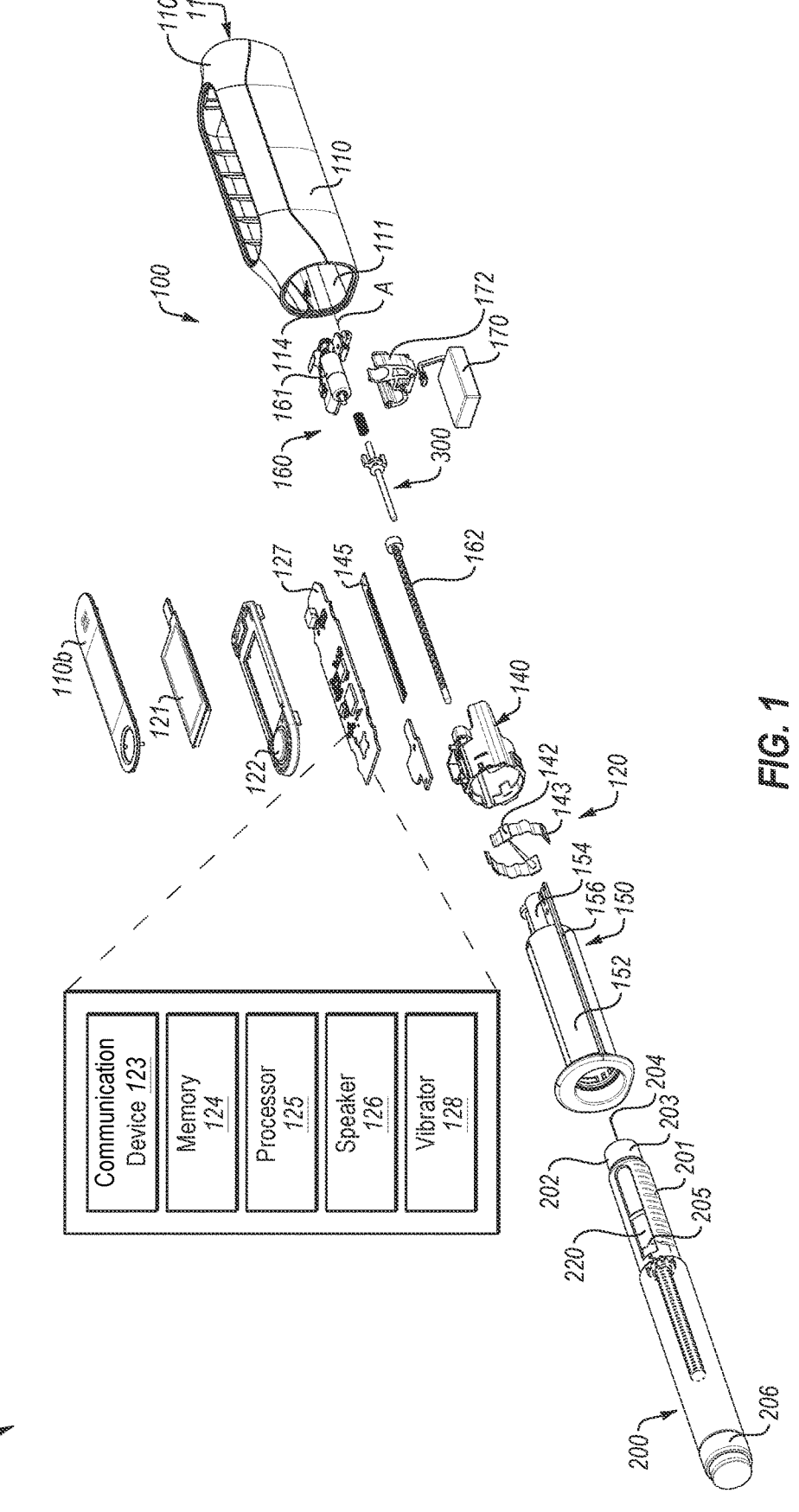
FIG. 1 is a perspective exploded view of an example liquid delivery system.

Referring to FIGS. 1 and 2A-C, an example liquid delivery system 10 is shown that can be used to store and deliver a liquid, and output dosage information to a user. The liquid delivery system 10 includes a cap device 100 and a liquid delivery device 200. The cap device 100 is positionable over at least a part of the liquid delivery device 200 for storage of the liquid delivery device 200 between uses. In an example embodiment, the cap device 100 includes one or more sensors configured to detect a position of the liquid delivery device 200 and/or a condition of liquid delivery device 200 (e.g., a position of its plunger). The cap device 100 can further include one or more output devices, such as a display, communication system, etc., configured to output information related to the position of the liquid delivery device 200 and/or the condition of liquid delivery device 200.

The liquid delivery device 200 may be configured to deliver a measured dose of a liquid to a subject for the treatment of a medical condition. For example, the liquid delivery device 200 may be a pen injector for delivering a liquid, such as insulin, to manage diabetes. In an example embodiment, the liquid delivery device 200 includes a reservoir 201, a delivery end 202, a plunger 205, and a dial 206. The reservoir 201 contains a liquid which can be injected at the delivery end 202. The delivery end 202 provides a portion over which the cap device 100 can be positioned to store the liquid delivery device 200 between uses. The delivery end 202 of the liquid delivery device 200 includes a septum 203 and an injection needle 204. The plunger 205 that can be operated to deliver a dose of the liquid with the reservoir 201 through the delivery end 202. For example, a desired dosage may be measured by operation of the dial 206 (e.g. by manually rotating the dial 206), and delivered by advancing the plunger 205. Advancement of the plunger 205 via a rod (not shown) pushes the measured dosage of liquid from the reservoir 201, through the delivery end 202, and into the subject. In an example embodiment, advancement of the plunger 205 a particular distance causes a corresponding volume of liquid to be dispensed from the liquid delivery device 200.

The cap device 100 may include a body 110, one or more sensors 120, interface components 130, a sensor carriage 140, a sleeve 150, and a motorized drive system 160.

The body 110 is configured to house various components of the cap device. The body 110 defines a cavity 111 configured to receive at least a portion of the liquid delivery device 200, such as at least a portion of the delivery end 202 and/or the reservoir 201. The cap device 100 is positionable over the delivery end 202 and may retain the liquid delivery device 200 (e.g., between periods of use). The cap device 100 may protect the delivery end 202 from damage or contaminants of the external environment, and contain the injection needle 204. The liquid deliver device 200 may be removed from the cavity 111 of the cap device 100 before each use, and subsequently engaged with the cap device 100 after a dose has been delivered. The cap device 100 may thus be removed from and replaced onto the liquid delivery device 200 over multiple uses. After the contents of a particular liquid delivery device 200 has been exhausted, the liquid delivery device 200 may be discarded, and the cap device 100 may be used with a new liquid delivery device. In some example embodiments, the liquid delivery device 200 is disposable when its usable contents are exhausted, and the cap device 100 may be reusable with multiple liquid delivery devices 200. In other example embodiments, the cap device 100 may be associated with a particular liquid delivery device 200, and both the cap device 100 and the liquid delivery device 200 may be disposed when the contents of the reservoir 201 are exhausted. In other example embodiments, the cap device 100 may be associated with a particular liquid delivery device 200, and the liquid delivery device 200 may refilled when the contents of the reservoir 201 are exhausted or the reservoir 201 replaced.

In various example embodiments, the body 110 is a molded body, such as a molded plastic. The body 110 may include multiple body portions that are assembled to form the body 110, such as a main body portion 110*a* and a cover portion 110*b*. In other example embodiments, the body 110 may be made as a single piece that defines the cavity 111.

One or more of the sensors 120 in the cap device 100 are configured to detect a position of the liquid delivery device 200 within the cap device 100. In an example embodiment, the cap device 100 includes one or more sensors that output sensor signals that may be evaluated to detect axial and/or radial positions of the liquid delivery device 200 with respect to the cap device 100. For example, the sensors can be used to determine that the liquid delivery device 200 are engaged in predetermined axial and/or radial positions relative to the cap device 100, thereby allowing accurate measurement of the condition of the liquid delivery device 200.

In addition, one or more of the sensors 120 can further detect a condition of the liquid delivery device 200. In an example embodiment, the cap device 100 includes one or more sensors 120 that output sensor signals that may be evaluated to detect the plunger 205, a position of the plunger 205, a change in position of the plunger 205 between successive engagements with the cap device 100 (e.g. a change in position after delivery of a dose), and/or other conditions of the liquid delivery device 200. The position of the plunger 205, and/or the change in the position of the plunger 205, may be used to monitor a volume of a dose delivered by the liquid delivery device 200, a remaining total volume of the liquid within reservoir 201, a remaining number of doses within the reservoir 201, a remaining duration until the reservoir 201 is emptied, and/or other information related to the liquid delivery device 200.

In some embodiments, at least one of the sensors for detecting the condition of the liquid delivery device 200 can be configured to further detect the position of the liquid delivery device 200. In other embodiments, the sensor(s) for detecting the condition of the liquid delivery device 200 can be different from the sensor(s) for detecting the position of the liquid delivery device 200. For example, the sensors 120 may include multiple sensors, such as a first sensor 142 and a second sensor 143. In some embodiments, the first sensor 142 is used to detect the position (e.g., radial position) of the liquid delivery device 200 and the second sensor 143 is used to detect the condition of the liquid delivery device 200. In some embodiments, the first sensor 142 is used to detect the position (e.g., radial position) of the liquid delivery device 200 and the first sensor 142 and/or the second sensor 143 may be used to detect the condition of the liquid delivery device 200. For example, the first sensor 142 or the second sensor 143 may be used to detect the condition of the liquid delivery device 200 depending on which sensor is positioned along a predetermined line of sight based on the radial position of the liquid delivery device 200. Alternatively or in addition, both of the first and second sensors 142, 143 may be used together to corroborate one another and promote a reliable determination of a condition of the liquid delivery device 200. In some embodiments, the condition of the liquid delivery device 200 may be detected only when the liquid delivery device 200 is detected to be arranged in a predetermined position (e.g., axial and/or radial alignment). For example, the sensors are not used to detect the condition of the liquid delivery device 200 until the liquid delivery device 200 is detected to be arranged in a predetermined position. In other embodiments, the condition of the liquid delivery device 200 may be detected before, or regardless of whether, the liquid delivery device 200 is arranged in the predetermined position (e.g., axial and/or radial alignment).

The sensor detecting an axial position (e.g., an axial alignment) can be a sensor that detects engagement with a snap feature or the types of sensors that detect whether the cap device is secured to the liquid delivery device. As described below, the cap device can include a mechanical feedback device (e.g., a spring-biased axial post 302 configured to provide a clicking or snap-in sensation when engaged), and a sensor coupled to the mechanical feedback device (e.g., a mechanical switch or other types of sensors configured to detect when the spring-biased axial post is engaged by the liquid delivery device). Examples of the sensors for axial position detection are further described in U.S. Pat. No. 8,743,662 and U.S. Provisional Application No. 62/667,085, the disclosures of which are incorporated hereby in their entireties to the extent appropriate.

The sensor detecting a radial position (e.g., a radial alignment) can be a sensor that detects engagement with a snap feature that permits for the liquid delivery device to snap-fit into the cap device in a predetermined radial position. As described below, the cap device can include a mechanical structure (e.g., a radial retention structure 800 having a detent 802) configured to radially secure the liquid delivery device and generate a mechanical feedback (e.g., a clicking or snap-in sensation when engaged). Further, the cap device can include a sensor, such as a mechanical switch or other types of sensors, configured to detect when the mechanical structure is properly engaged by the liquid delivery device.

The sensors that detect an axial position and/or a radial position can be of various types, such as optical sensors, mechanical switches, or other suitable types that determine such positions of the liquid delivery device relative to the cap device.

In various example embodiments, the first sensor 142 and the second sensor 143 are the same type of sensor. In some example embodiments, the first sensor 142 differs from the second sensor 143 in one or more characteristics. For example, the first sensor 142 may have a different sensor resolution or precision than the second sensor 142. For example, the first sensor 142 for detecting the position of the liquid delivery device 200 may have a lower sensor resolution or precision than the second sensor 143 for detecting the condition of the liquid delivery device 200. A lower resolution or precision may facilitate a reduced overall cost of cap device 100 and/or enhanced calibration efficiency, for example. In some embodiments, either the first sensor 142 or the second sensor 143 (or both) may be used to detect both the position and condition of the liquid delivery device 200.

At least one of the sensors 120 may be supported by the sensor carriage 140 that is movably arranged in the cap device 100. For example, the first and second sensors 142 and 143 are carried by, and movable with, the sensor carriage 140 while a position sensor 145 is fixedly arranged within the cap device 100. The position sensor 145 may be configured to detect an axial position or distance of the sensor carriage 140 with respect to the cap device 100.

The sensors 120, such as the first and second sensors 142 and 143, are configured to output a sensor signal representative of a characteristic of the liquid delivery device 200. The output signal from a sensor may vary depending on a physical characteristic of the liquid delivery device 200 encountered by the sensor, and thus the output signal may differ at different axial and/or radial positions relative to the liquid delivery device 200. For example, as the liquid delivery device 200 rotates relative to the cap device 100 (e.g., while a user positions the cap device 100 on the liquid delivery device 200), a change in the output signal of a sensor (e.g., the sensor 142) may be evaluated to determine one or more predetermined features (e.g., a distal edge or chamfer of a reservoir window) of the liquid delivery device 200, which may indicate that the liquid delivery device 200 is in a predetermined position (e.g., a predetermined radial alignment). Further, as the sensor carriage 140 moves relative to the liquid delivery device 200, a change in the output signal of a sensor (e.g., the sensor 142 and/or the sensor 143) may be evaluated to determine a leading edge of a leading end of the reservoir 201 (e.g. at the delivery end 202), a leading end of the plunger 205, a trailing end of the plunger 205, and/or other attributes of the liquid delivery device 200. A change in position detected between a series of doses, such as a change in position of the plunger 205 before and after a dose has been delivered, may be used to evaluate a volume of a dose delivered by the liquid delivery device 200, a remaining total volume of liquid within the reservoir 201, a remaining number of doses within the reservoir 201, a remaining duration until the reservoir 201 is emptied, a time of the previous dose (e.g. a time the cap device 100 was replaced on the liquid delivery device 200), an elapsed time since the last dose (e.g. an elapsed time since the cap device 100 was replaced on the liquid delivery device 200), and/or other information related to the liquid delivery device 200. Alternatively or additionally, the relative positions of one or more of these detected characteristics, or a distance between one or more of these detected characteristics, may be used to evaluate dosage information related to the liquid delivery device 200.

In an example embodiment, the sensor 142 includes an emitter 142*a* and a receiver 142*b*, such as an optical emitter 142*a* and optical receiver 142*b*. The optical emitter 142*a* emits radiation that can be detected by the optical receiver 142*b*, and in some embodiments may include an LED or laser diode. The sensor 142 may output a sensor signal related to the amount of radiation received by the optical receiver 142*b* (e.g. an amount of radiation received from the optical emitter 142*a*). The sensor signal may thus depend on the features of the liquid delivery device 200 present in a path 142*c* (e.g., FIGS. 2A-2C) between the optical emitter 142*a* and the optical received 142*b*. The amount of radiation received by the optical receiver may thus be relatively lower when a different structure, a plunger, or other solid structure is present in the path 142*c*, and may be relatively higher when only transparent walls of a reservoir and its liquid contents are present in path 142*c*, for example.

The emitter 142*a* and the receiver 142*b* may be arranged in alignment with one another such that an optical path 142*c* between the emitter 142*a* and the receiver 142*b* extends perpendicular (e.g. substantially perpendicular, within 10° of exactly perpendicular) to the central longitudinal axis A of the cavity 111. In some embodiments, the emitter 142*a* is configured to generate a narrow beam with limited spread outside of the optical path 142*c*, such as by an emitter 142*a* that emits a narrow beam and/or by a collimating structure configured to focus the output of the emitter 142*a* along the path 142*c*. In various example embodiments, radiation emitted by the emitter 142*a* may be within visible and/or invisible wavelengths.

In some example embodiments, the sensor 142 may be a reflective sensor that detects reflected light. The reflective sensor 142 may detect a color transition indicative of the plunger 205, such as transition from a relatively higher transparency and/or light color of liquid and/or reservoir 201 to the relatively lower transparency and/or dark color of the plunger 205 (e.g. red, orange, black, etc.).

In an example embodiment, the sensor 143 may be configured similarly to the sensor 142, including an emitter 143*a* and a receiver 143*b* that define a path 143*c*.

Referring still to FIG. 1, the interface components 130 of the cap device 100 include various components that facilitate calculation, display, storage, and/or communication of sensor signals that may be output by the sensors 120. In an example embodiment, the interface components 130 include a display 121, a user input device 122, a communication interface 123, a memory 124, a processor 125, a speaker 126, and a vibrator 128. One or more components may be in electrical communication with one or more other components via a circuit board 127. The processor 125 may be configured with logic to control operation of one or more of the components and to process sensor signals received from the sensors 120 of the cap device 100. At least one of the interface components and other components may be housed in the housing 110.

In some embodiments, the display 121 provides a visual output to a user related to a position of the liquid delivery device 200 relative to the cap device 100, and/or a condition of the liquid deliver device 200 and/or the cap device 100. The display 121 may be an LED or LCD display, for example. In some embodiments, the display 121 may provide a visual indication related to axial and/or radial positions of the liquid deliver device 200 relative to the cap device 100. Further, the display 121 may be provide a visual indication related to a volume of a dose delivered by the liquid delivery device 200, a remaining total volume of liquid within the reservoir 201, a remaining number of doses within the reservoir 201, a remaining duration until the reservoir 201 is emptied, a time of the previous dose (e.g. a time the cap device 100 was replaced on the liquid delivery device 200), an elapsed time since the last dose (e.g. an elapsed time since the cap device 100 was replaced on the liquid delivery device 200), and/or other information related to the liquid delivery device 200.

Alternatively or additionally, the cap device 100 may include audio and/or vibratory alerts related to a position of the liquid delivery device 200 relative to the cap device 100, and/or a condition of the cap device 100 and/or the liquid delivery device 200. The processor 125 may control audio output of the speaker 126 to output an audible alert, or the vibrator 128 to output a vibratory alert, which may be perceived as an indication of axial and/or radial positions of the liquid delivery device 200 relative to the cap device 100. Further, such audible or vibratory alerts may be used to provide an indication of a volume of a dose delivered by the liquid delivery device 200, a remaining total volume of the liquid within reservoir 201, a remaining number of doses within the reservoir 201, a remaining duration until the reservoir 201 is emptied, a time of the previous dose (e.g. a time the cap device 100 was replaced onto the liquid delivery device 200), an elapsed time since the last dose (e.g. an elapsed time since the cap device 100 was replaced onto the liquid delivery device 200), and/or other information related to the liquid delivery device 200. Alternatively or additionally, the vibrator 128 may deliver vibrations to the liquid delivery device 200. The vibrator 128 may be activated to facilitate mixing of the contents of the liquid delivery device 200 and/or to reduce the formation or buildup of precipitates (e.g. on the leading surface of plunger and/or surfaces of the reservoir 201).

The user input device 122 is configured to facilitate user interaction with the cap device 100. In an example embodiment, the user input 122 includes one or more buttons, switches, or other control interfaces that may be operated to control the cap device 100. For example, the user input device 122 may be operated by a user to activate the cap device 100 and/or select information to be displayed by the display 121. As described herein, in some implementations, the cap device 100 can be automatically activated by engagement with the liquid delivery device 102. Alternatively or additionally, the user input device 122 may be operated to reset settings and/or the memory 124 of the cap device 100, such as when the cap device 100 is engaged with a new liquid delivery device 200. In some example embodiments, the cap device 100 does not include the user input device 122. The cap device 100 that does not include a user input device may promote the perception of a fully automated cap device 100 and/or improve user operability.

The cap device 100 may communicate with one or more other components of a liquid delivery system to deliver and/or receive information related to a position of the liquid delivery device 200 relative to the cap device 100, and/or a condition of the cap device 100 and/or the liquid delivery device 200. For example, the communication device 123 of the cap device 100 is configured to communicate with one or more components remote from the cap device 100. The communication device 123 may include a wireless communication printed circuit assembly configured for wireless communication, such as via short-wavelength UHF radio frequency, RF communication, WI-FI, BLUETOOTH, ZIG-BEE, etc. Alternatively or additionally, the communication device 123 may include an electrical port for wired communication with another electronic device. In various example embodiments, the communication device 123 is configured for two-way communication, such as two-way communication with a mobile device having software configured to deliver and receive communications with the cap device 100. Alternatively, the cap device 100 may be configured for one-way communication, such as only to upload information to the mobile device, or only to receive information from the mobile device.

The communication device 123 may be configured to communicate with an electronic device configured with diabetes management software. For example, the communication device 123 may transmit information related to the liquid delivery device 200 that may be further processed by the electronic device. In this way, the cap device 100 may facilitate review of information collected by its sensors by a remote user or healthcare provider, provide alerts related to the liquid delivery system 200 by the electronic device (e.g. related to a scheduled time for an injection, a nearly empty liquid delivery device, etc.), and/or facilitate additional processing and analysis of the information collected by the cap device 100.

The cap device 100 may include a power source 170. In an example embodiment, the power source 170 comprises one or more batteries, such as alkaline batteries, nickel cadmium batteries, lithium ion batteries, etc. In some embodiments, the power source 170 is associated with an axial position device 300 configured to be activated when engaged with a portion of the liquid delivery device 200 being axially inserted into the cap device 100. When activated, the axial position device 300 can operate to switch the cap device 100 between an inactive or low power state to an active or operational state in which sensors of the cap device 100 are active. In other embodiments, the power source 170 may be associated with a micro-switch configured to switch the cap device between the inactive or low power state to the active or operational state. Alternatively or additionally, a sensor signal from one or more sensors of the cap device 100, such as one or more position sensors, may provide an alert to the processor 125 to switch the cap device to the active or operational state.

Referring still to FIG. 1, the sensor carriage 140 of the cap device 100 is configured to carry one or more of the sensors 120, and is movably positioned within the cavity 111 of the body 110. In some embodiments, the sensor carriage 140 is configured to axially travel along at least a portion of the liquid delivery device 200 within the cavity 111. The cavity 111 can be sized to accommodate the dimensions of the liquid delivery device 200 and a path for the sensor carriage 140.

The sensor carriage 140 facilitates detection of characteristics, such as position and/or condition of the liquid delivery device 200 by carrying one or more sensors along the liquid delivery device 200 between a first position and a second position. In an example embodiment, the sensor carriage 140 is movable between the first position and the second position relative to the cavity 111 while the liquid delivery device 200 remains in a fixed position relative to the cavity 111 (e.g. the sensor carriage 140 is movable while the liquid delivery device 200 is fixedly engaged with cap device 100). Such example movable positions of the sensor carriage 140 are illustrated and described in more detail with reference to FIGS. 2-4 below.

The sensor carriage 140 may include multiple sensors, such as the first and second optical sensors 142 and 143. In some implementations, one of the multiple sensors (e.g., one of the first and second optical sensors 142 and 143) can be used to detect a radial position of the liquid delivery device relative to the cap device. For example, as described above, the first sensor 142 is configured to detect a radial position of the liquid delivery device, and the second sensor 143 is configured to detect a condition of the liquid delivery device (e.g., the plunger position).

The first optical sensor 142 includes the first emitter 142a and the first receiver 142b, and the second optical sensor 143 includes the second emitter 143a and the second receiver 143b. The first emitter 142a may be aligned with the first receiver 142b and the second emitter 143a aligned with the second receiver 143b (e.g. such that the first receiver 142b receives radiation primarily or exclusively from the first emitter 142a and the second receiver 143b receives radiation primarily or exclusively from the second emitter 143a). For example, the first emitter 142a and the second receiver 143b, and the second emitter 143a and the first receiver 142b, are not in alignment and do not define an optical path perpendicular to the longitudinal axis of the cavity 111. Alternatively, the first emitter 142a may be aligned with the second receiver 142b for sensing, and/or the second emitter 143a may be aligned with the first receiver 143b for sensing. In an example embodiment, the first and second emitters 142a, 143a, and the first and second receivers 142b, 143b, are spaced 90° from each other around a perimeter of the sensor carriage 140. Accordingly, the first sensor 142 and the second sensor 143 may define the first and second paths 142c, 143c oriented perpendicular to one another. In some embodiments, the first path 142c and/or the second path 143c do not intersect with a central longitudinal axis of the cavity 111 or a central longitudinal axis of the liquid delivery device 200. The first and/or second paths 142c, 143c that do not intersect the central axis may facilitate detection of a trailing surface 205b of the plunger 205 by avoiding obstruction by the rod of the plunger. Although the first sensor 142 and the second sensor 143 are primarily described as optical sensors, either or both of them can be other types of sensors.

For example, the first sensor 142 that may be configured to detect the radial position of the liquid delivery device can be configured as a mechanical switch usable to determine whether the liquid delivery device is snapped in a predetermined radial position within the cap device.

In various example embodiment, the relative radial location of sensor 142 relative to the liquid deliver device 200 can determine if there is an appropriate line of sight through the reservoir 201 that determines an accurate determination of the position of the plunger 205, which can be used to determine an amount of liquid remaining in the liquid delivery device. Some embodiments of the cap device are configured to be compatible with various types of liquid delivery devices, each of which may have a variety of features (e.g., ribs, indicia, bumps, numbers, hash lines, and other obstructions) in different locations. Depending on the radial position of the liquid delivery device relative to the cap device, the locations of such features may block or distort the light from emitter 142a so that the leading edge and/or rear edge of the plunger 205 is obscured or difficult to determine, thus affecting the reliability of the determination of an amount of liquid remaining in the liquid delivery device 200 and/or the reliability of a determination of a dose of liquid from the liquid delivery device 200. The radial alignment position(s) can be determined such that such features of each liquid delivery device do neither block the sensor(s) from detecting the plunger, nor distort the view of the plunger. The radial alignment position(s) for the liquid delivery device relative to the cap device provides an optimal optical path across the reservoir along the entire length of the reservoir so that the plunger can be viewed and detected in any of its positions along the length of the reservoir.

In some embodiments in which multiple optical sensors 142, 143 are present, distinct wavelengths may be emitted by each emitter 142a, 143a, and receivers 142b, 143b may likewise be wavelength-specific, for example, by including a bandpass filter. Alternatively or additionally, each sensor may emit and detect pulses of radiation in distinct time periods of a cycle (e.g. using time-division multiplexing). In some embodiments, sampling rates may be greater than 100 Hz, greater than 1000 Hz, or higher.

Alternatively or additionally to the sensors 142, 143, the sensor carriage 140 may include a position sensor 145 configured to output a sensor signal indicative of a position or distance. In an example embodiment, the cap device 100 includes a position sensor 145 that outputs a sensor signal indicative of a position of the sensor carriage and/or distance the sensor carriage traveled between a first position and a second position (e.g. as the sensor carriage 140 moves along the liquid delivery device 200 or between subsequent doses of the liquid delivery device 200). In an example embodiment, the position sensor 145 includes a linear potentiometer. A resistive element is located at least partially along a length of cavity 111, such as a side wall of the body 110 or the sleeve 150. A wiper may be located on the sensor carriage 140.

The position sensor 145 may output a sensor signal (e.g. a voltage) that varies depending on the position of the wiper along the resistive element (e.g. and a position of the sensor carriage 140 along the cavity 111). For example, a particular voltage may be associated with a particular location along the resistive element, and the voltage may be consistent and repeatable each time the wiper travels along the resistive element. The sensor 145 may have a unique signature of voltage outputs for each location of the wiper, and can be calibrated to achieve highly precise and repeatable measurements.

Alternatively or additionally to a linear potentiometer, the position sensor 145 may include one or more other sensor types that provide an indication of position that can be correlated with an sensor signal output by the sensor 142 and/or the sensor 143. For example, the position sensor 1145 may include a linear encoder, rotary encoder, magnetic potentiometer, membrane potentiometer, load cell, etc., for example.

Referring still to FIG. 1, the sleeve 150 of the cap device 100 is configured to be arranged at least partially within the cavity 111 of the body 110, and receive at least a portion of the liquid delivery device 200. The sleeve 150 may include a main wall 152 and a front wall 154 extending axially from the main wall 152 and configured to receive the delivery end 202 and/or the injection needle 204 of the liquid delivery device 200. The sleeve 150 at least partially surrounds the injection needle 204 (e.g. proximate a front of the cap device 100) and the reservoir 201 between the injection needle 204 and the opening 114 of the body 110. The sensor carriage 140 may be movable between the sleeve 150 and an interior wall of the body 110, and the sleeve 150 can be positioned between the liquid delivery device 200 and the sensor carriage 140 during operation of the sensor carriage 140.

Alternatively or additionally, the sleeve 150 may include one or more retention features that engage with the liquid delivery device 200 and limit axial and/or radial movements the liquid delivery device 200 relative to the body 110 of the cap device 100. Examples of the retention features may include an axial position device 300, a portion of the sleeve 150 (e.g., a flange wall 158 thereof), and a radial retention structure 800, as described herein.

In some embodiments, the sleeve 150 includes a track 156 configured to guide and/or limit the movement of the sensor carriage 140. In an example embodiment, the track 156 is configured as one or more rails that engage with complementary features (e.g., axial recesses) of the sensor carriage 140. In the illustrated example, the track 156 includes two rails axially extending along at least a portion of the length of the sleeve 150 and arranged oppositely on the exterior of the sleeve 150. The track 156 defines a path that the sensor carriage 140 travels along, such as in a longitudinal direction between a first position proximate to a front wall 112 of the body 110 and a second position closer to an opening 114 of the body 110.

The motorized drive system 160 operates to drive the sensor carriage 140 along a longitudinal axis of the cap device 100, such as along a longitudinal axis extending centrally through the front wall 112 and the opening 114 of the body 110. For example, the motorized drive system 160 includes a motor 161 and a leadscrew 162 connected, directly or indirectly, to a drive shaft of the motor 161. The motor 161 can be mounted to a motor mount block 172 that is placed in the cavity 111 and proximate to the front wall 112 of the body 110. Rotation of the leadscrew 162 caused by operation of the motor 161 results in axial movement of the sensor carriage 140. Rotation of the motor 161 in a first direction results in movement of the sensor carriage 140 towards the opening 114 of the cavity 111 and rotation of the motor 161 in a second opposite direction results in movement of the sensor carriage 140 towards the front wall 112 of the body 110. In an example embodiment, the motorized drive system 160 can thus drive the sensor carriage 140 between any number of discrete points along the leadscrew 162.

Although it is primarily described in this document that the cap device 100 is operated with the motorized drive system 160, it is understood that the principles and configurations of the present disclosure are similarly applicable to other types of cap devices, such as non-motorized cap devices.

Figure 2A:
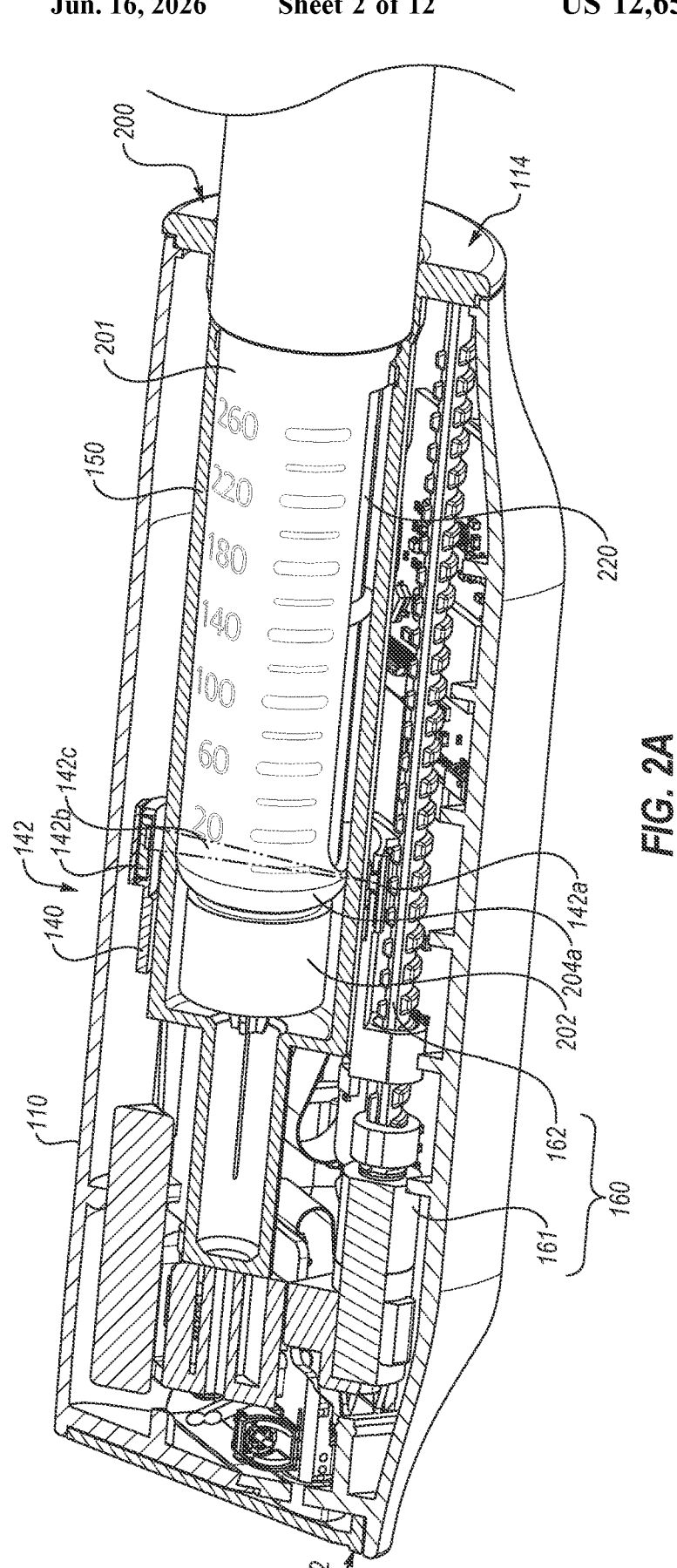
FIG. 2A is a perspective partial cross sectional view of the liquid delivery system with a sensor carriage in a first position.
Figure 2B:
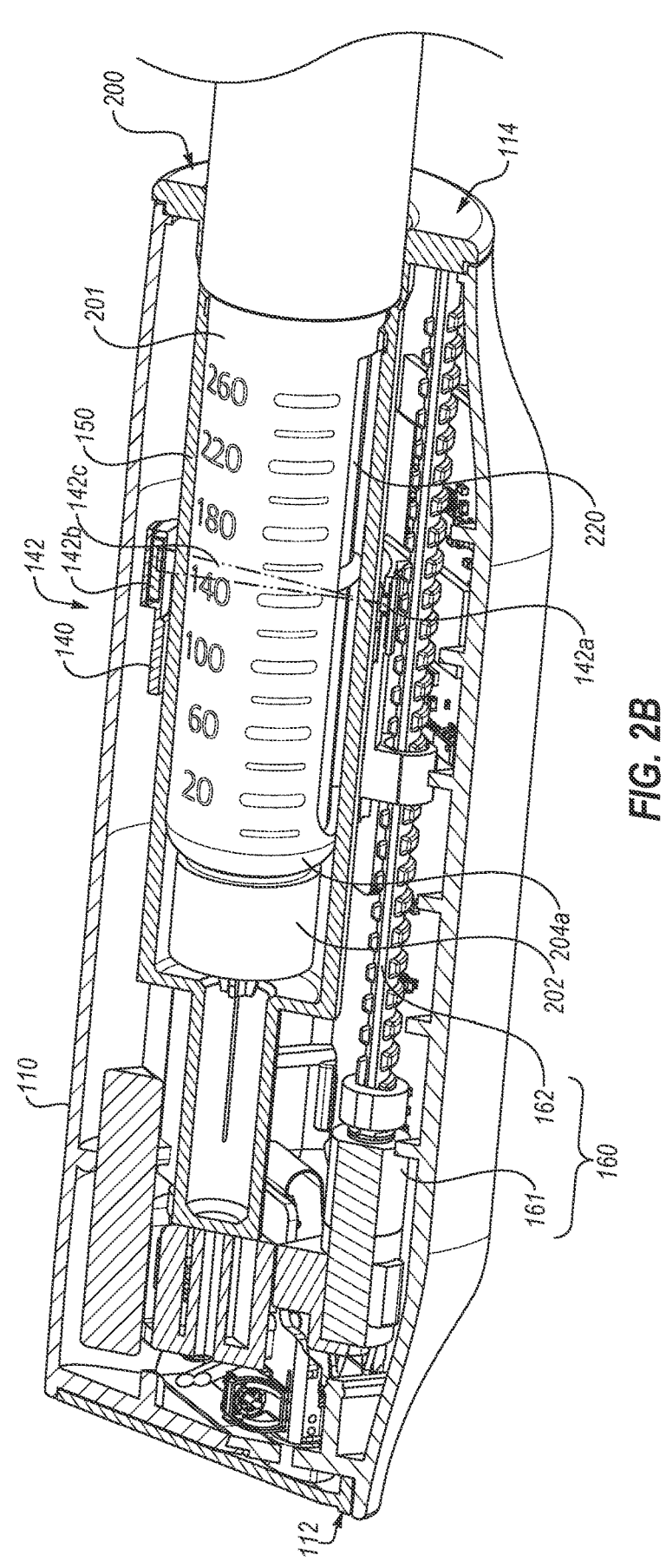
FIG. 2B is a perspective partial cross sectional view of the liquid delivery system with a sensor carriage in an intermediate position.
Figure 2C:
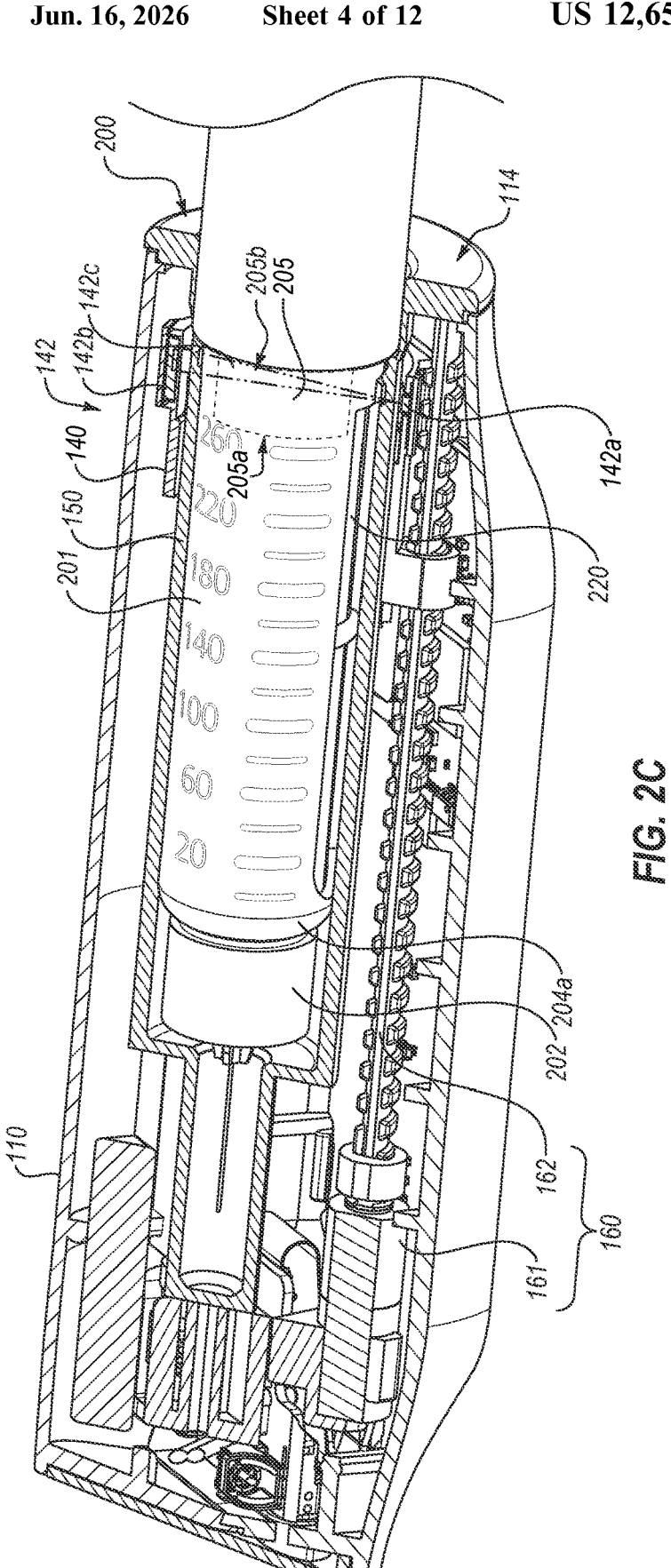
FIG. 2C is a perspective partial cross sectional view of the liquid delivery system with a sensor carriage in a second position.

Referring now to FIGS. 2A, 2B, and 2C, the movable sensor carriage 140 is shown in a first position (FIG. 2A), an intermediate position (FIG. 2B), and a second position (FIG. 2C). The sensor carriage 140 is movable to any position from the first position to the second position or vice versa while the liquid delivery device 200 is at least partially received within the body 110. In some embodiments, the sensor carriage 140 is movable between the first position and the second position while the liquid delivery device 200 remains fixedly positioned relative to the body 110 of the cap device 100. Movement of the sensor carriage 140 between the first and second positions facilitates detection of characteristics of the liquid delivery device 200 at multiple locations of the liquid delivery device 200. The sensors 142 and 143 may generate output signals continuously or at a relatively high frequency (e.g. between 0.1 and 100 kHz, between 5 and 50 kHz, or about 30 kHz) while the sensor carriage 140 moves between the first and second positions. In some embodiments, operation of the sensors 142 and 143 as the sensor carriage 140 travels between the first and second positions can be described as generating a scan of a portion of the liquid delivery device 200, and the output signals from the sensors 142 and 143 (e.g. alone or in conjunction with one or more sensors, such as a position sensor 145) can be evaluated to determine a position of the plunger 205 within the reservoir 201, a change in position of the plunger 205 within the reservoir 201, and/or other conditions of the liquid delivery device 200.

In addition or alternatively, the sensor carriage 140 is movable to a predetermined position (i.e., a radial alignment detection position) in which the sensor 142 of the sensor carriage 140 is configured to detect a radial position of the liquid delivery device 200 that is engaged with the cap device 100. As described herein, when the sensor carriage 140 is arranged at the radial alignment detection position between the first and second positions, the sensor 142 of the sensor carriage 140 may operate to detect a predetermined feature (e.g., one of opposite axial tips, edges, and/or other features of a window 220 formed in the reservoir 201) of the liquid delivery device 200 to determine that the liquid delivery device 200 is in a desired radial position (i.e., a radial alignment position) with respect to the cap device 100.

In some embodiments, the radial alignment detection position of the sensor carriage 140 is arranged adjacent to the first position (FIG. 2A). In other embodiments, the radial alignment detection position is identical to the first position. In yet other embodiments, the radial alignment detection position is arranged adjacent to, or identical to, the second position (FIG. 2C). In yet other embodiments, the radial alignment detection position can be any position between the first and second positions.

The sensor carriage 140 may be configured to be initially arranged at various positions in different embodiments. In one example embodiment, the sensor carriage 140 may be configured to be arranged at the first position as a default position and return to the first position after one or more operations at different positions. Alternatively or additionally, the sensor carriage 140 may be configured to be arranged at the radial alignment detection position as a default position and return to the radial alignment detection position after one or more operations at different positions.

In some embodiments, the sensor carriage 140 may be configured to be arranged at the second position as a default position and return to the second position after one or more operations at different positions. In yet another embodiment, other positions of the sensor carriage 140 can be used as default positions.

The sensor carriage 140 may return to its default position at any time, such as shortly after the liquid delivery device 200 is engaged with the cap device 100, after one or more predetermined processes (e.g., a scan process that the sensor carriage 140 moves between the first and second positions to detect a position of the plunger 205) are complete, and/or shortly after the liquid delivery device 200 is removed from the cap device 100.

In the first position shown in FIG. 2A, the sensor carriage 140 is located proximate the front wall 112 of the body 110. In some embodiments, the sensor carriage 140 may be brought into the first position by the operation of inserting the liquid delivery device 200 within the cavity 111. In other embodiments, the sensor carriage 140 is arranged at the first position by default before the liquid delivery device 200 is inserted into the cavity 111.

The sensor carriage 140 can be movable from the first position towards the second position by the motorized drive system 160. The sensor 142 of the sensor carriage 140 may output sensor signals as the sensor carriage 140 travels between the first and second positions along the liquid delivery device 200. In the first position shown in FIG. 2A, the field of view 142c (e.g., or optical path or line of sight) between the emitter 142a and the receiver 142b intersects the delivery end 202 of the liquid delivery device 200, or a portion of the liquid delivery device 200 adjacent the delivery end 202. The sensor signals may be evaluated (e.g. by the processor 125) to detect the presence of a leading end of the reservoir 201. In some embodiments, a particular magnitude of the sensor signal, or an increase in the magnitude of the sensor signal, may thus provide an indication of the leading end of the reservoir 201.

FIG. 2B shows the sensor carriage 140 in an intermediate position between the first and second positions. The field of view 142c between the emitter 142a and the receiver 142b passes through an intermediate location of the reservoir 201. The wall of the reservoir 201, and the liquid within the reservoir 201, may provide relatively lower opacity to transmission of radiation between the emitter 142a and the receiver 142b, such that the sensor signals are relatively higher in the intermediate position.

FIG. 2C shows the sensor carriage 140 in the second position in which the sensor carriage 140 is located proximate the opening 114 of cavity 111. In the second position, the sensor carriage 140 has traveled beyond a leading surface 205a of the plunger 205 such that the field of view 142c intersects the plunger 205. The presence of the leading surface 205a may be detected by a change in the sensor signal at a location the field of view 142c encounters the leading surface 205a. For example, a magnitude of radiation received by the receiver 142b may be reduced or stepped down due to the presence of the plunger 205 in the path 142c.

The sensor 142 may continue to detect characteristics of the liquid delivery device 200 after traveling beyond the leading surface 205a of the plunger 205. For example, a trailing surface 205b may be detected based on a change in the sensor output at a location that the trailing surface 205b intersects the path 142c. For example, a magnitude of radiation received by the receiver 142b may be increased or stepped up due to the absence of the plunger 205 intersecting the path 142c. The length of the plunger 205 between the leading surface 205a and the trailing surface 205b is fixed and thus either the leading surface 205a or the trailing surface 205b may be used to evaluate a position of plunger 205. Detecting both the leading and trailing surfaces 205a, 205b of the plunger 205 may improve the accuracy in evaluating the plunger 205. For example, the position of the plunger 205 may be accurately located even if a leading or trailing surface 205a, 205b is obstructed by another feature of the liquid delivery device 200, such as a rib, indicia, etc.

The position of the plunger 205 or a change in position of the plunger 205 may be evaluated in conjunction with sensor signal output by the position sensor 145. In an example embodiment, the sensor signals generated by the position sensor 145 vary in a predictable manner as the sensor carriage 140 moves between the first position and the second position. For example, a sensor signal of the position sensor 145 for a particular location may be associated with a sensor signal from the sensor 142 at the particular location. A change in position of the plunger 205 before and after a dose has been delivered may be detected, and the volume of the delivered dose calculated based on the change in position. Alternatively or additionally, a distance between locations associated with various output signals from the sensor 142 may be evaluated, such as a distance between a leading end of the reservoir 201 and a leading surface 205a of the plunger 205, and the remaining volume with the reservoir 201 calculated based on the distance.

Figure 3:
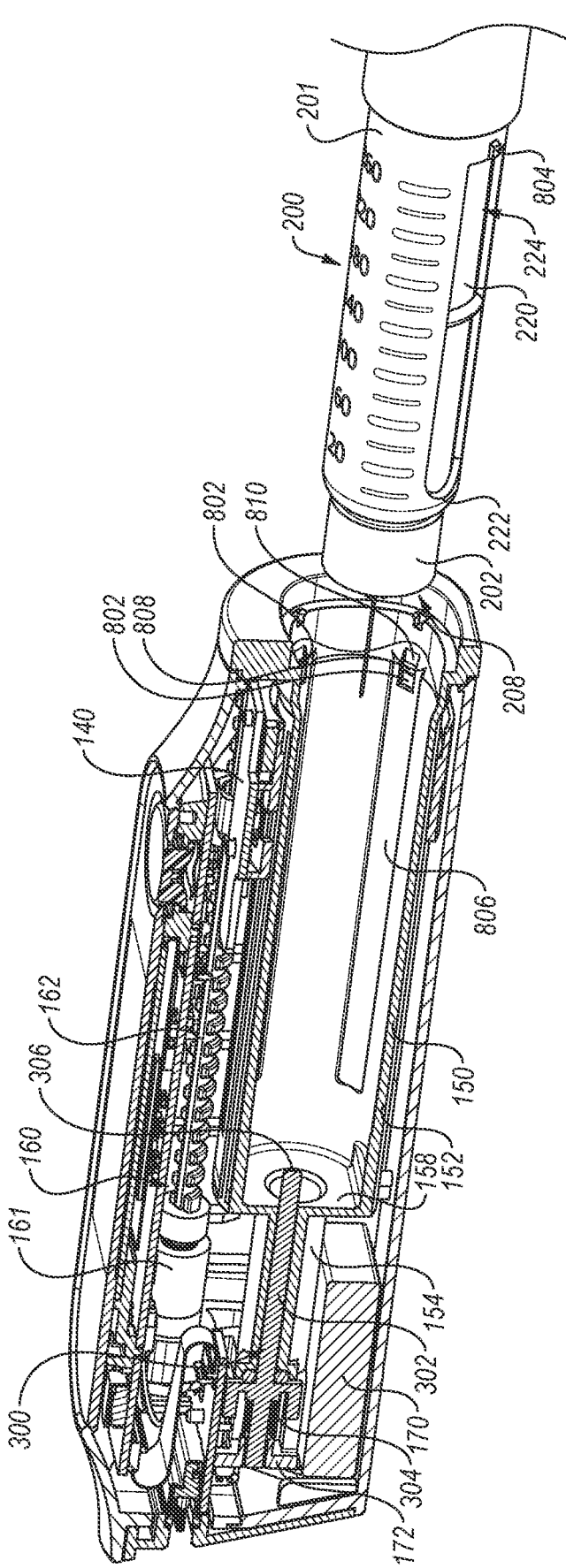
FIG. 3 is a perspective partial cross sectional view of the liquid delivery system with a liquid delivery device out of engagement with a cap device.

Referring FIG. 3, an example axial position device 300 is shown while the liquid delivery device 200 is not located within into the body 110 of the cap device 100. The axial position device 300 is configured to engage a portion of the liquid delivery device 200 as the liquid delivery device 200 is axially inserted into the cap device 100. The axial position device 300 is configured to provide a mechanical feedback when the liquid delivery device 200 is inserted into a predetermined axial position within the cavity 111 of the body 110. For example, the sleeve 150 includes a flange wall 158 formed between the main wall 152 and the front wall 154 and configured to engage with a forward end 208 (e.g., the delivery end 202) of the liquid delivery device 200 to limit the axial movement of the liquid delivery device 200 within the cavity 111 of the body 110. The axial position device 300 is configured to provide a mechanical feedback to a user who is gripping the liquid delivery device 200 and/or the cap device 100, as the forward end of the liquid delivery device 200 is about to engage with the flange wall 158 of the sleeve 150.

In some embodiments, the axial position device 300 may include a longitudinal post 302 that is movably mounted to the motor mount block 172. A spring 304 can be engaged between a rear portion of the post 302 and a portion of the motor mount block 172 to bias the post 302 against the motor mount block 172 (i.e., towards the cavity 111 or the sleeve 150 in a direction opposite to the direction in which the liquid delivery device 200 is inserted). A distal end 306 of the post 302 extends through the flange wall 158 of the sleeve 150 and into a space surrounded by the main wall 152 of the sleeve 150. Thus, the forward end 208 of the liquid delivery device 200 becomes to contact with the distal end 306 of the post 302 and pushes the post 302 against the biasing force of the spring 304. In some embodiments, the post 302 can be pushed back against the spring 304 until the forward end 208 of the liquid delivery device 200 is abutted with the flange wall 158 of the sleeve 150.

In addition or alternatively, the axial position device 300 is configured to detect an axial engagement of the liquid delivery device 200 with the cap device 100. For example, the axial position device 300 includes one or more switches or sensors configured to detect the post 302 being pushed by the liquid delivery device 200, and for generating sensor signals indicative of the axial engagement of the liquid delivery device 200 relative to the cap device 100 (e.g., the sleeve 150). In response, the cap device 100 may be activated/powered on, and/or initiate one or more operations, such as detection of a radial position of liquid delivery device 200.

Figure 4:
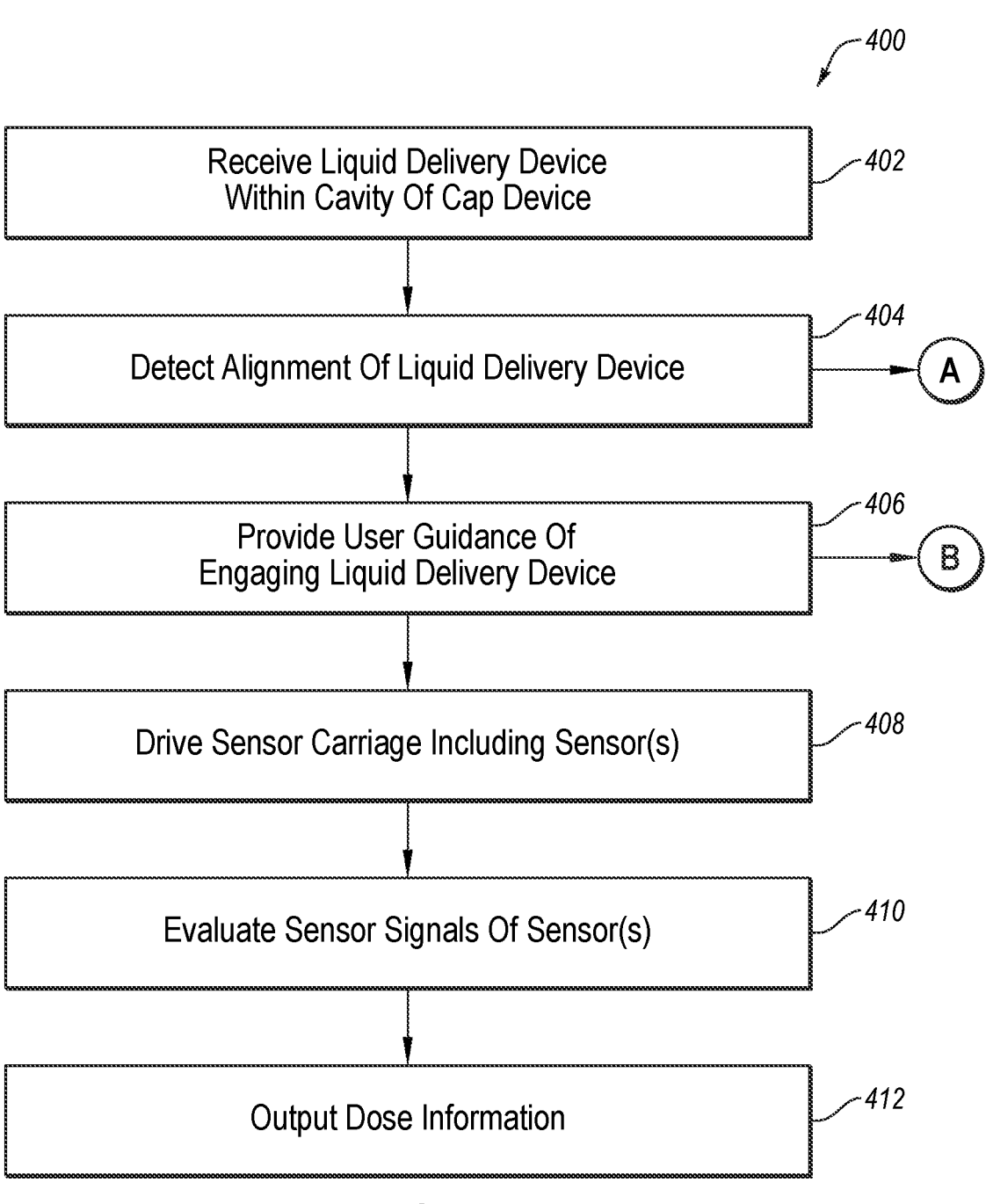
FIG. 4 is a flow diagram of an example method of detecting alignment and condition of a liquid delivery device.

Various example cap devices described herein facilitate effective, repeatable techniques of evaluating a position (e.g., alignment) and/or condition of a liquid delivery device. Referring to FIG. 4, a flow diagram of an example method 400 of detecting the alignment and condition of a liquid delivery device is shown. The method 400 includes operation 402 of receiving at least a portion of a liquid delivery device within a cavity of a cap device. In various example embodiments, the liquid delivery device may have features and characteristics similar to the liquid delivery device 200 described herein, and may be a pen-injector device for administering a dose of insulin. The cap device may have features and characteristics similar to the cap device 100 described herein.

The operation 402 may include axially inserting into the cavity of the cap device and/or radially rotating the liquid delivery device relative to the cap device, until the liquid delivery device is axially engaged/aligned and/or radially aligned, such as aligning a central longitudinal axis of the liquid delivery device with a central longitudinal axis of the cavity of the cap device, and/or aligning a radial position of the liquid delivery device with respect to the cavity of the cap device. Alternatively or additionally, the liquid delivery device may be aligned into one or more discrete axial and/or radial alignment positions with the cap device. For example, the liquid delivery device and/or the cap device may have an asymmetrical feature, non-circular shape, and/or other mechanical/geometric feature that facilitates receiving the liquid delivery device in one or more discrete positions (e.g., selected based on predetermined locations of one or more sensors within the cap device). Alignment of the liquid delivery device with the cap device in a particular orientation can facilitate desired interaction between one or more sensors of the cap device and the liquid delivery device by reducing interference or obstruction by ribs, indicia, opaque regions, and/or other features.

In an example embodiment, the operation 402 of receiving the liquid delivery device with the cavity of the cap device may include fixedly engaging the cap device with the liquid delivery device. For example, after the operation 402, relative motion between the liquid delivery device and the cap device may be limited such that the liquid delivery device is not rotatable within the cavity and/or the liquid delivery device is not movable longitudinally within the cavity.

The method 400 includes operation 404 of detecting an alignment of the liquid delivery device. The operation 404 may include detecting the liquid delivery device is rotated into a predetermined radial position (e.g., a radial alignment position) with respect to the cap device. The predetermined radial position may be one or more positions that facilitate accurate detection of the position and movement of the plunger in the liquid delivery device by the sensors of the sensor carriage in the cap device. Alternatively or in addition, in some embodiments, the operation 404 may include determining the liquid delivery device is inserted into the cap device and placed at a predetermined axial position (i.e., an axial alignment position). For example, the cap device includes one or more sensor that generates sensor signals when the liquid delivery device is engaged with the cap device at such a predetermined axial position. The predetermined axial position may be a position that permits the liquid delivery device to come into the predetermined radial position when rotated at the predetermined axial position. In other embodiments, the operation 404 does not include the detection of the liquid delivery device coming into the predetermined axial position. The cap device may be configured to provide a mechanical feedback (e.g., an axial resistive force) as the liquid delivery device approaches the predetermined axial position, and/or to provide an axial structure that stops the axial movement of the liquid delivery device over the predetermined axial position when axially inserted into the cap device.

When the liquid delivery device is in the predetermined alignment position, the liquid delivery device remains fixedly engaged with the cap device. A relative motion between the liquid delivery device and the cap device may be limited such that the liquid delivery device is not rotatable within the cavity and/or the liquid delivery device is not movable longitudinally within the cavity. An example operation 404 is further described herein, such as with reference to FIG. 5.

In some embodiments, the radial alignment position may include a plurality of radial alignment positions, each providing a predetermined line of sight for accurate plunger detection. In other embodiments, the radial alignment position may be a single radial alignment position that provides such a predetermined line of sight for accurate plunger detection. Where multiple sensors are employed, such multiple sensors, such as the first and second sensors 142 and 143, are used to detect one or more of the plurality of radial alignment positions.

Figure 9:
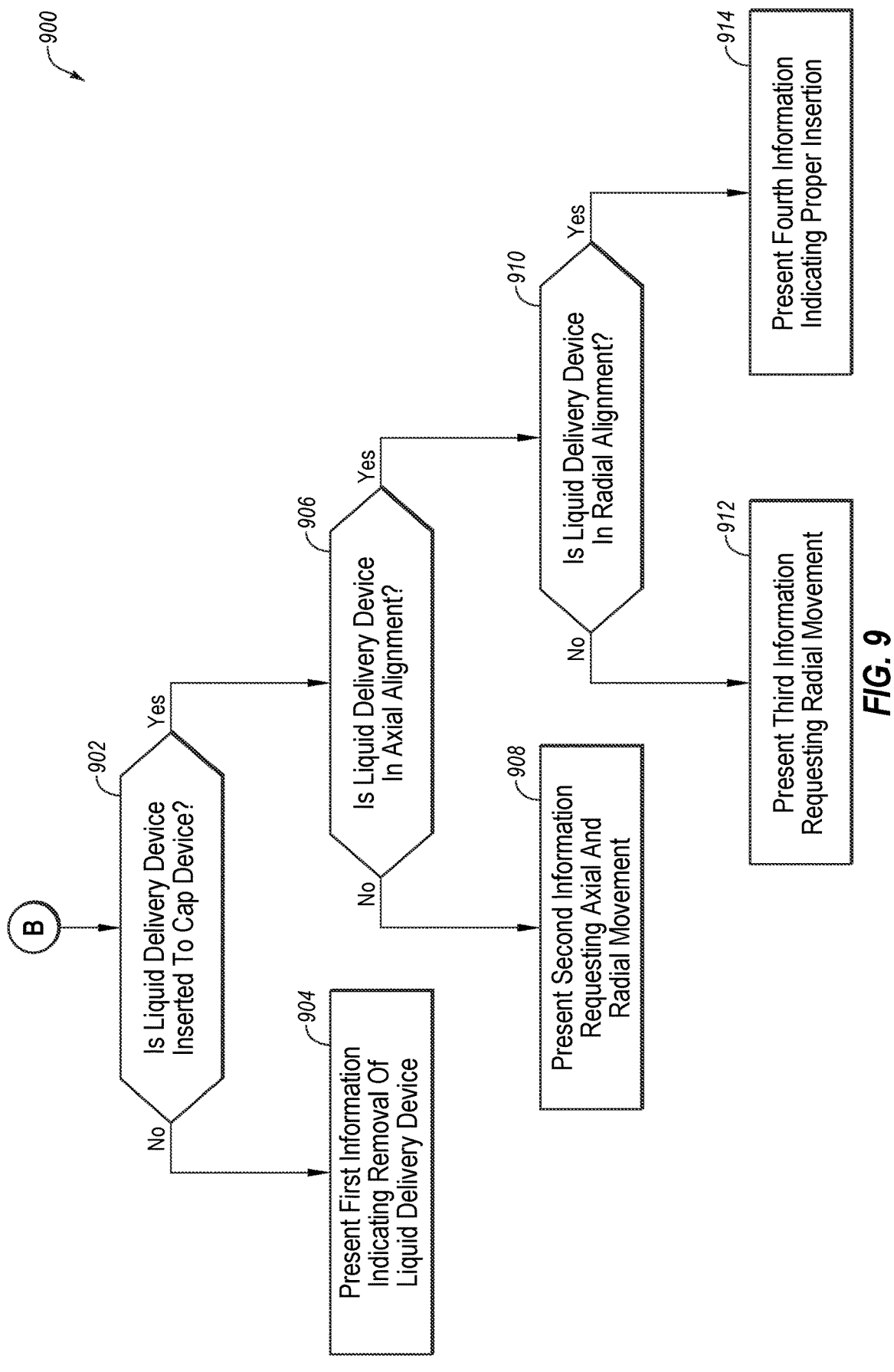
FIG. 9 is a flowchart of an example method for displaying information on a cap device.

The method 400 includes operation 406 of providing user guidance to assist the user to engage the liquid delivery device with the cap device at a predetermined alignment position (e.g., axial and/or radial alignment position). In some embodiments, the cap device includes an output device, such as a display screen, that presents one or more symbols (e.g., signs, texts, letters, numbers, etc.) that indicate a positional status of the liquid delivery device relative to the body. For example, the cap device can display symbols representative of steps to engage the liquid delivery device with the cap device into a predetermined alignment position. In some embodiments, the cap device displays such symbols until the liquid delivery device is detected at such a predetermined alignment position. The steps may include first axially inserting the liquid delivery device at least partially into the cap device until the liquid delivery device is arranged at the predetermined axial position (e.g., placing the cap device 100 on to the liquid delivery device 200 such that they snap together), and then rotating the liquid delivery device relative to the cap device until the liquid delivery device is detected at the predetermined radial position. For example, there may be corresponding snap features in the cap device 100 and the liquid delivery device 200 such that they snap into the predetermined radial alignment upon the user rotating the cap device 200 relative to the liquid delivery device 200 towards the predetermined radial alignment. An example operation 406 is further described herein, such as with reference to FIG. 9.

In some implementations, the operation 406 may include determining that the liquid delivery device is arranged in a predetermined position relative to the cap device (e.g., a position that enables accurately monitoring the position of a plunger, thereby allowing an accurate determination of the amount of the content remaining in the liquid delivery device), and providing the guidance based on such determination. For example, the operation 406 may include actively monitoring the position of the liquid delivery device relative to the cap device either over time or at intervals, and determine whether the liquid delivery device is in an axial and/or radial alignment relative to the cap device.

The method 400 may include operation 408 of driving a sensor carriage including one or more sensors (e.g., sensor 142). The operation 404 may include driving the sensor carriage by a motorized drive system including an electric motor. For example, the motorized drive system may drive the sensor carriage from a first position to a second position or vice versa. One or more sensor signals located on the sensor carriage operate while the sensor carriage moves between the first and second positions to output sensor signals indicative of one or more features of the liquid delivery device.

In some example embodiments, the operation 408 is performed on the condition that the liquid delivery device is in the predetermined alignment position relative to the cap device as determined at the operation 404. Alternatively or additionally, the operation 408 may be performed even if the liquid delivery device is not determined to be in the predetermined radial alignment position relative to the cap device, but in the predetermined axial position, to determine if the position of the plunger can be detected even if the determination is less accurate than if the liquid delivery device is in the predetermined radial alignment. In some embodiments, the operation 408 may be performed both before the liquid delivery device is determined to be in the predetermined radial alignment position relative to the cap device and again after the liquid delivery device is determined to be in the predetermined radial alignment position. In some cases, operation 408 may be time delayed after the liquid delivery device is placed in the predetermined axial position to provide the user sufficient time to rotate the liquid delivery device 200 relative to the cap device 100 to achieve the predetermined radial alignment, but may conduct operation 408 after a predetermined amount of time after being placed in the predetermined axial position even if the cap device 100 is not in the predetermined radial alignment. If a user then later rotates the cap device 100 relative to the liquid delivery device 200 to achieve the predetermined radial alignment, the cap device 100 can perform operation 408 again to determine the position of the plunger and an amount of liquid remaining in the liquid deliver device 200. The subsequent results from operation 408 after having the predetermined radial alignment may be compared to the earlier results outside of the predetermined radial alignment, and/or used to correct, corroborate, update, replace, etc., the earlier results.

In some example embodiments, the operation 408 of driving the sensor carriage may be initiated without additional manual operation. For example, the cap device may detect engagement with the liquid delivery device, such as by a sensor, and initiate operation of the motorized drive system after detecting the liquid delivery device.

The operation 408 may optionally include driving the sensor carriage in multiple directions. For example, the motorized drive system may drive the sensor carriage in one or more back and forth movements, such as to obtain multiple measurements over a particular location or locations. The sensor carriage may be driven by the motorized drive system, including in back and forth directions, while the liquid delivery device remains fixedly positioned relative to the cap device, and/or without additional manual intervention, for example.

The method 400 may further include operation 410 of evaluating an output of the one or more sensors indicative of the presence of a feature of the liquid delivery device. For example, the cap device may include a processor configured to evaluate sensor signals from one or more of the sensors, such as a variation in sensor signals indicative of the plunger, and to determine a corresponding position. In some embodiments, the operation 410 may include storing the corresponding position and comparing the corresponding position during subsequent capping events. Evaluating the sensor signals may including evaluating a change in position to determine the volume of the previous dose delivery (e.g. by evaluating the distance traveled by the plunger), a remaining volume within the liquid delivery device, or other characteristics of the liquid delivery device.

In some embodiments, the method 400 may include operation 412 of outputting information related to the position of the plunger. Information may be output by the cap device and/or transmitted to one or more remote devices. For example, the operation 412 may include displaying the previously delivered dose. Alternatively or additionally, the operation 412 may include displaying dose information related to a remaining total volume of liquid within the reservoir of the liquid delivery device, a remaining number of doses within the reservoir of the liquid delivery device, a remaining duration until the reservoir of the liquid delivery device is emptied, a time of the previous dose (e.g. a time of the operation 402 of receiving the liquid delivery device within the cavity), an elapsed time since the last dose (e.g. an elapsed time since the operation 402 of receiving the liquid delivery device within the cavity), and/or other information related to the liquid delivery device.

In the illustrated exemplary embodiment, the operations 408, 410, and 412 are illustrated to be performed after at least one of the operations 404 and 406. For example, the cap device can detect a physical feature (e.g., a plunger) of the liquid delivery device at a time when the liquid delivery device is in an appropriate radial alignment relative to the cap device. When a user has axially inserted the liquid delivery device but failed to rotate it to a radial alignment position (e.g., forgot to do so, positioned out of alignment, etc.) (e.g., at time A), the cap device may wait until the liquid delivery device is later rotated to the radial alignment position (e.g., at time B), and operate to detect a condition associated with the liquid delivery device. In various exemplary embodiments, the cap device may output information/indicators (e.g., just before time B) to prompt the user to move the liquid delivery device to the radial alignment position. For example, the cap device may output information/indicators to prompt the user to move the liquid delivery device to the radial alignment position, even if the cap delivery device was engaged with the liquid delivery device in a misaligned position several minutes, hours, or days earlier, and/or if the display has subsequently turned off (e.g., turned off between time A and time B).

Alternatively, at least one of the operations 408, 410, and 412 may be performed before or during at least one of the operations 404 and 406. For example, when the liquid delivery device is not radially aligned, the cap device may still operate to detect the physical feature of the liquid delivery device, and later rerun a detection process once the liquid delivery device is rotated to the radial alignment position, thereby updating the previous detection. For example, information related to a condition of the liquid delivery device determined at an earlier time (e.g., such as liquid volume within the reservoir, dosage information, volume of a previously delivered dose, other information related to the liquid delivery device and its operation) can be updated. In some example embodiments, the cap device may output further information and/or engage in subsequent operations, such as output information related to an insulin-on-board determination, recommend a correction dose, etc.

In some embodiments, the cap device may operate to log time of measurements, detections, or other events associated with the liquid delivery device. For example, the cap device can record time of detecting the position of the plunger. In another example, the cap device can log time before, when, and/or after the liquid delivery device is moved into axial and/or radial alignment positions relative to the cap device.

Figure 5:
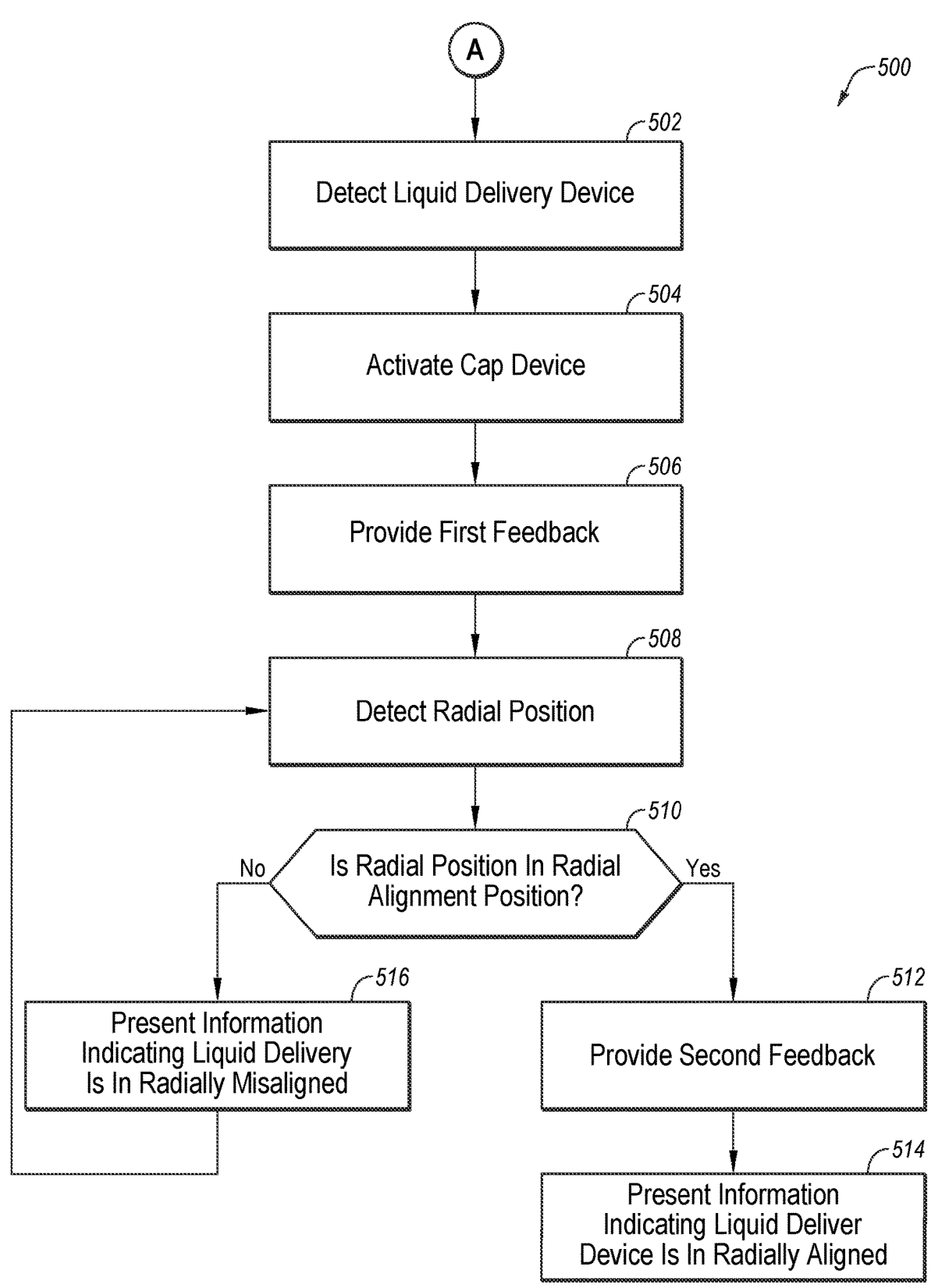
FIG. 5 is a flow diagram of an example method of detecting engagement and/or alignment of a liquid delivery device relative to a cap device.
Figure 6A:
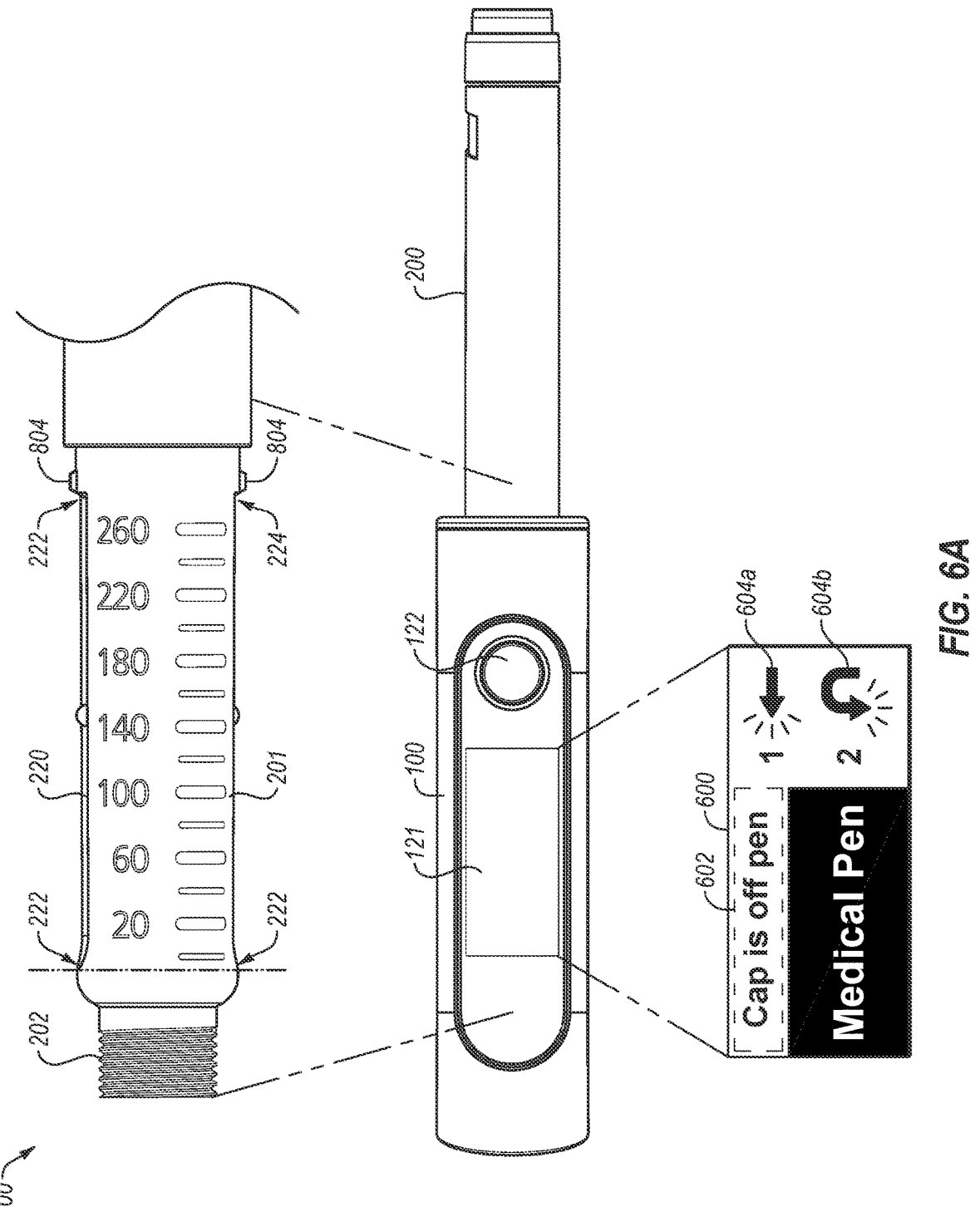
FIG. 6A schematically illustrates an example position of a liquid delivery device relative to a cap device, and an example display interface of the cap device.
Figure 6B:
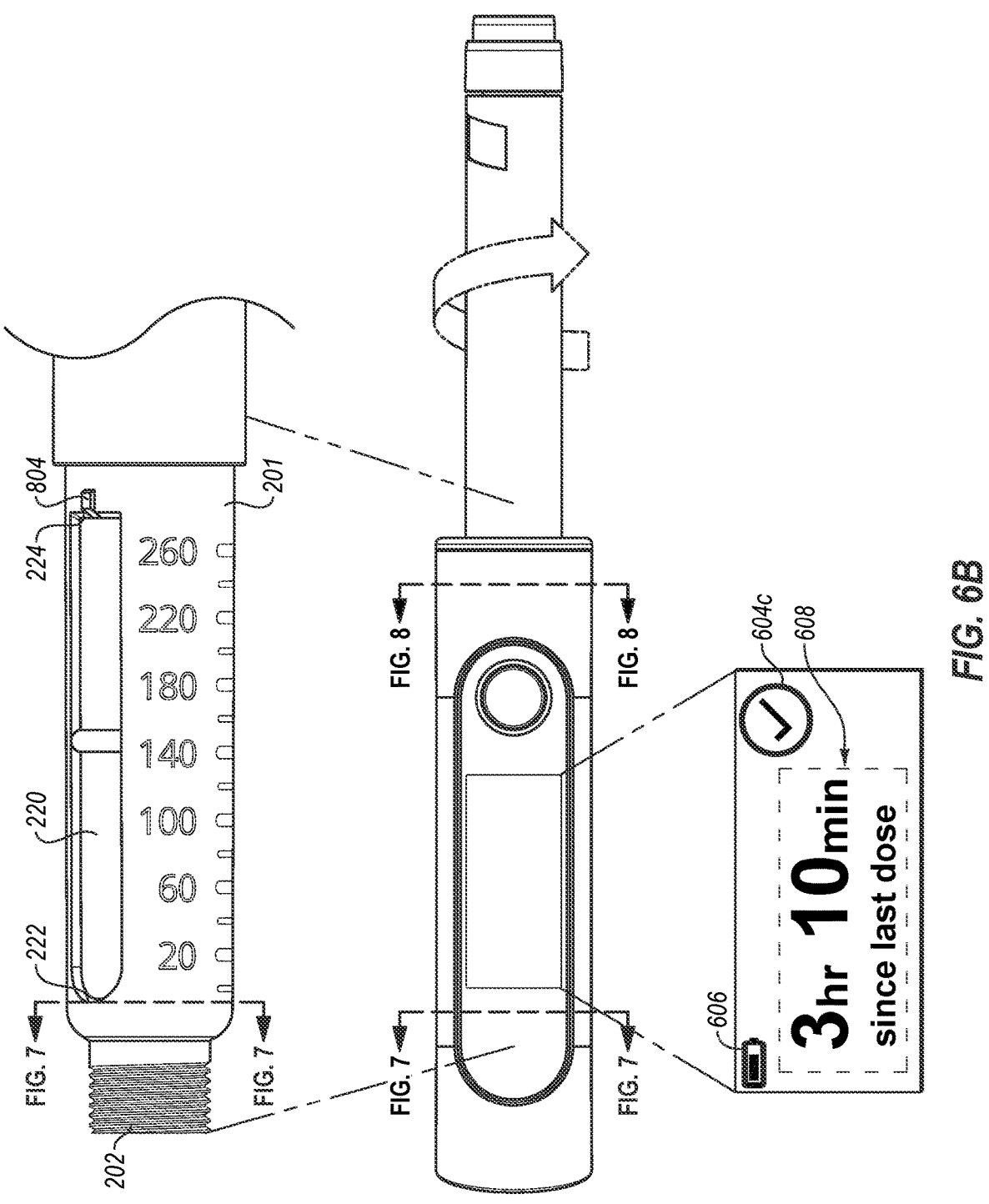
FIG. 6B schematically illustrates another example position of a liquid delivery device relative to a cap device, and another example display interface of the cap device.

Referring to FIGS. 5, 6A, and 6B, an example method 500 of detecting engagement and/or alignment of the liquid delivery device relative to the cap device is described. The method 500 can be used to perform the operation 404 described in FIG. 4.

Referring to FIG. 5, some embodiments of the method 500 may include operation 502 of detecting that the liquid delivery device is axially inserted to an axial alignment position in the cap device. In some embodiments, the axial alignment position can be a furthest end in the cavity of the cap device (or in the sleeve 150 (FIG. 3) of the cap device) to which the liquid delivery device can be inserted. For example, a furthest end wall (e.g., the flange wall 158 in FIG. 3) can limit an axial insertion of the liquid delivery device and defines an axial alignment position of the liquid delivery device. In other embodiments, the axial alignment position can be another position within the cavity of the cap device, such as one or more axial positions between the furthest end and the opposite open end of the cavity (or in the sleeve 150 (FIG. 3) of the cap device).

In the operation 502, the detection of the axial alignment of the liquid delivery device can include a detection that the cap device is axially inserted, and secured, onto the liquid delivery device, regardless of whether the cap device is in a radial alignment.

In other embodiments, the operation 502 may be optional, and the cap device does not operate to detect the axial position of the liquid delivery device relative to the cap device.

The method 500 may include operation 504 of activating the cap device. In some embodiments, the cap device is automatically switched from an inactive or low power state to an active or operational state when the liquid delivery device is engaged with the cap device and/or arranged in the predetermined axial alignment position. Engagement between the liquid delivery device and the cap device, and/or activation of the cap device based on engagement, may serve as an indicator of the liquid delivery device in the axial alignment position. The cap device can be configured to be automatically activated when the liquid delivery device is at least partially inserted into the cap device regardless of the axial and/or radial position of the liquid delivery device. In some embodiments, the cap device is automatically activated when the liquid delivery device is determined to be arranged at the axial and radial alignment positions. Alternatively or additionally, the cap device is manually activated by a user via a user input device (e.g., a power button).

The method 500 may include operation 506 of providing a first feedback to indicate that the liquid delivery device is in the axial alignment position. For example, the first feedback can be a mechanical feedback that is generated by a resistive spring force from an axial position device. The axial position device may be spring-biased in a direction opposite to a direction in which the liquid delivery device is inserted, and configured to engage a portion of the liquid delivery device as the liquid delivery device is axially inserted into the cap device. After the liquid delivery device first interacts (e.g., contacts) the axial position device, the liquid delivery device can be further inserted to push against the biasing force of the axial position device up to certain point (e.g., up to a predetermined axial alignment position). Such an interaction can cause a mechanical feedback (e.g., a clicking sensation) passing through the liquid delivery device and/or the cap device, and the user who is holding the liquid delivery device and/or the cap device by, e.g., fingers, can feel the feedback. Examples of detecting an axial position and providing a feedback are described in U.S. Pat. No. 8,743,662 and U.S. Provisional Application No. 62/667, 085, the disclosures of which are incorporated hereby in their entireties to the extent appropriate.

Alternatively or in addition, the first feedback can be generated in other manners. For example, the first feedback is electrically generated and output in various formats, such as visible and/or audible formats, via a display device and/or a speaker in the cap device.

The method 500 may include operation 508 of detecting a radial position of the liquid delivery device relative to the cap device. As illustrated in FIGS. 6A and 6B, the liquid delivery device can be arranged at a radial alignment position relative to the cap device in two steps. For example, the liquid delivery device can be axially inserted to an axial alignment position relative to the cap device (Step 1 in FIG. 6A), and then at least partially rotated relative to the cap device (Step 2 in FIG. 6B). The cap device may include one or more sensors to detect when the cap device is in the predetermined radial alignment, and determine whether the liquid delivery device is in the radial alignment position relative to the cap device. In some embodiments, this detection may be done by one or more of the sensors that are supported by a sensor carriage and configured to detect a condition of the liquid delivery device, such as position and movement of the plunger in the liquid delivery device. In other embodiments, the cap device can be provided with other sensors located at a fixed position on the body of the cap device and/or dedicated for radial position detection. In addition, the sensor(s) in the cap device may be used to track the radial position of the liquid delivery device. An example of the operation 508 is further described with reference to FIGS. 6A and 6B below.

The method 500 may include operation 510 of determining whether the liquid delivery device is in the radial alignment position. If the liquid delivery device is determined to be at the radial alignment position ("YES") (e.g., in one or more predetermined radial alignment positions, ranges or positions, etc.), the method 500 may move on to operation 512. Otherwise ("NO"), the method 500 may continue at operation 516, which is described below.

The method 500 may include operation 512 of providing a second feedback to indicate that the liquid delivery device is in the radial alignment position. The second feedback can be a mechanical feedback that is generated by mechanical structures provided in the liquid delivery device and/or the cap device. Such mechanical structures may include mechanical detents, snaps, and other suitable mechanical interactions. For example, the cap device includes one or more detents formed in the sleeve and engagable with one or more corresponding projections formed in the liquid delivery device when the liquid delivery device is rotated into the radial alignment position. As the liquid delivery device rotates to the radial alignment position, the projections of the liquid delivery device slide into the detents of the cap device. A mechanical feedback (e.g., a clicking sensation) is generated and passed through the cap device and/or the liquid delivery device at the time that the projections of the liquid delivery device fit into (e.g., snap into) the detents of the cap device. The user who is holding the liquid delivery device and/or the cap device by, e.g., fingers, can feel the feedback. An example configuration for generating the second feedback is illustrated and described in further detail with reference to FIG. 8 below.

Alternatively or in addition, the second feedback can include other feedback. For example, the second feedback is electrically generated and output in various formats, such as visible and/or audible formats, via a display device and/or a speaker in the cap device The method 500 may include operation 514 of presenting information indicating that the liquid delivery device is in the radial alignment position. Such information can be presented to indicate to a user that the liquid delivery device is properly engaged with the cap device (e.g., for storage, subsequent operation, etc.). The information can be output in various formats. In some embodiments, a display device of the cap device can display one or more symbols (e.g., signs, texts, letters, numbers, etc.) that represent the liquid delivery device is radially aligned with the cap device. For example, as illustrated in FIG. 6B, a check mark can be displayed to confirm the radial alignment of the liquid delivery device. Other formats for outputting the information may include audible output via a speaker in the cap device or haptic output via a vibrator in the cap device, for example.

The method 500 may include operation 516 of presenting information indicating that the liquid delivery device is in radially misalignment. Such information can be used to assist the user to take an action to fix the misalignment, such as further turning the liquid delivery device radially relative to the cap device until the information disappears or until the user recognizes the second feedback indicative of the radial alignment position.

In the operation 516, in some implementations, the cap device can be configured to attempt to detect the position of the plunger if the radial misalignment remains over a threshold period of time. For example, while the radial misalignment is determined so that the radial position of the cap device continues to be detected, the cap device can take a measure of where the plunger is located to see if it can determine a dose amount or a remaining amount of content even if it may be inaccurate. As described herein, such a potentially-inaccurate measurement may be updated when the cap device is later determined to be into the radial alignment in which an accurate measurement can be obtained.

At the operation 516, the information can be presented in various formats. In some embodiments, a display device of the cap device can display one or more symbols (e.g., signs, texts, letters, numbers, etc.) designed to represent a misalignment status of the liquid delivery device. For example, as illustrated in FIG. 6A, one or two arrow marks can be displayed to indicate the steps to take to arrange the liquid delivery device in the alignment position relative to the cap device. Other formats for outputting the information are also possible, such as audible output via a speaker in the cap device or haptic output via a vibrator in the cap device.

Referring now to FIGS. 6A and 6B, in some embodiments, the liquid delivery device can be inserted and arranged in an alignment position in a sequence of steps (e.g., two steps). In the first step (Step A) (FIG. 6A), the liquid delivery device 200 can be axially inserted at least partially into the cap device 100 in any orientation. In the second step (Step B) (FIG. 6B), the liquid delivery device 200 can be rotated until the liquid delivery device 200 is in a radial alignment position.

In Step A, in some embodiments, the cap device 100 includes a structure (e.g., the axial position device 300) that provides a feedback (e.g., a mechanical clicking sensation) when the liquid delivery device 200 is inserted into a predetermined axial position. The predetermined axial position can be a position that the liquid delivery device 200 is fully inserted into the cap device (e.g., inserted at least partially into the cap device to the extent allowable by the structures of the liquid delivery device and/or the cap device). For example, as illustrated in FIG. 3, the sleeve 150 of the cap device 100 includes the flange wall 158 configured to engage with the forward end 208 of the liquid delivery device 200 and limit the axial movement of the liquid delivery device 200 within the cap device 100. The feedback can confirm that the liquid delivery device 100 is in the suitable axial position (e.g., fully inserted) and that the liquid delivery device is ready to be rotated into a radial alignment position in Step B.

In Step A, the liquid delivery device 100 can be axially inserted in any radial orientation. Unless the liquid delivery device 100 happens to be oriented in the radial alignment position relative to the cap device prior to being axially inserted, the liquid delivery device 100 that has been axially inserted to the cap device is not in the radial alignment position.

In some embodiments, when the liquid delivery device 100 is in the axial alignment position, the cap device 200 can be automatically switched from an inactive or power-saving state to an active or power-on state. In other embodiments, the cap device 200 can be manually turned on regardless of the axial and/or radial positions of the liquid delivery device 100.

Figure 8:
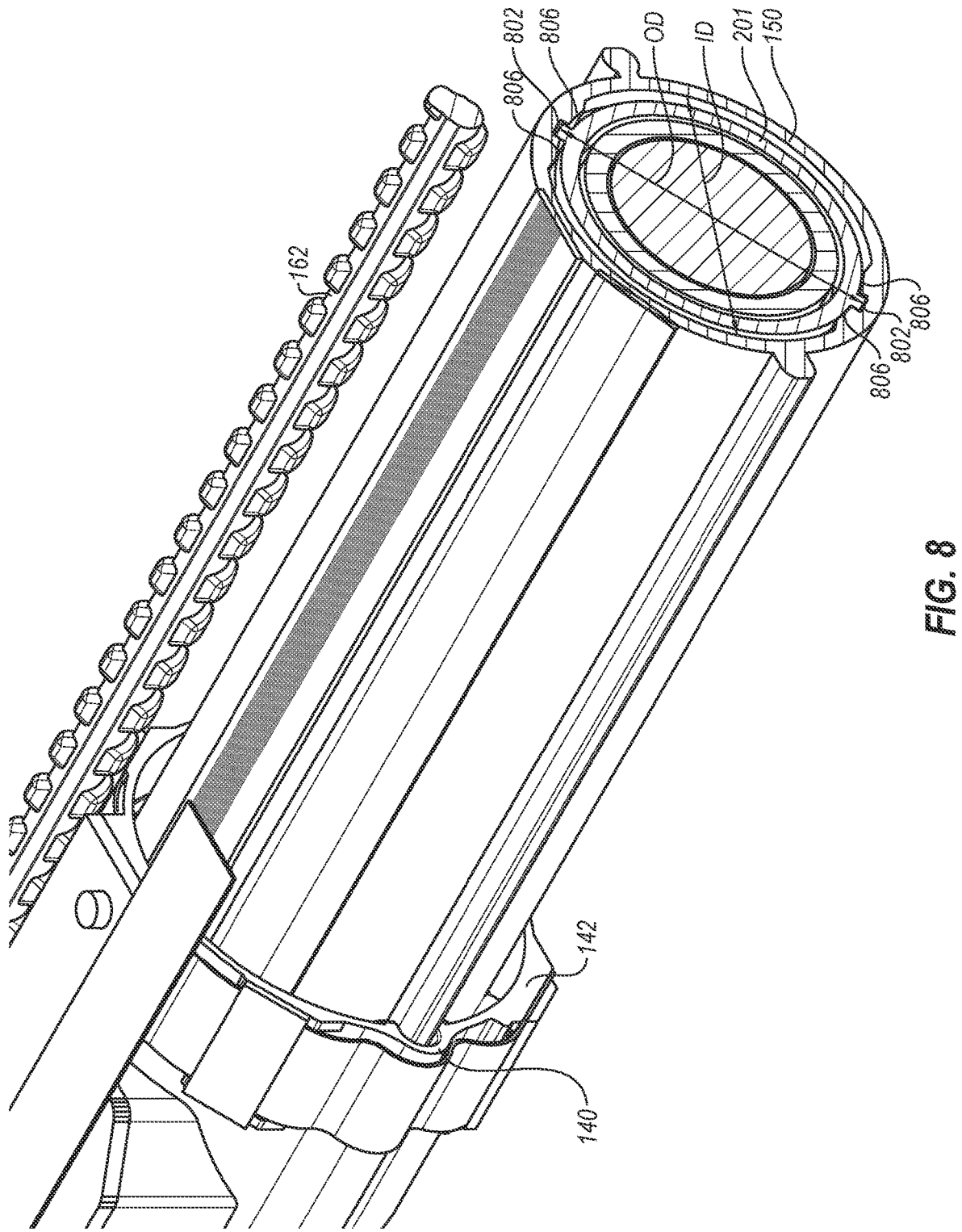
FIG. 8 is a perspective cross sectional view of a cap device and a liquid delivery device, illustrating an example feedback structure to generate a mechanical feedback indicative of a radial alignment of the liquid delivery device relative to the cap device.

In Step B, the liquid delivery device 200 can be radially rotated until it reaches to the radial alignment position. In some embodiments, the cap device 100 includes a structure (e.g., a detent and projection configuration) that provides a feedback (e.g., a mechanical clicking sensation) when the liquid delivery device 200 is in a predetermined radial position. The predetermined radial position can be an orientation of the liquid delivery device relative to the cap device that does not obstruct a field of view from the sensors in the cap device, facilitating the sensors to clearly detect a condition of the liquid delivery device, for example, such as position and/or movement of the plunger of the liquid delivery device. As illustrated in FIG. 8, the cap device 100 includes one or more detents 802 radially arranged on the inner surface of the sleeve 150, and the liquid delivery device 200 includes one or more projections 804 radially arranged on the exterior of the liquid delivery device 200 and configured to be complementary to the detents 802 of the cap device 100. The detents 802 and the projections 804 are arranged to be axially aligned when the liquid delivery device 200 is inserted into the axial alignment position relative to the cap device 100. When the detents 802 and the projections 804 are axially aligned and not radially engaged, it means that the liquid delivery device 200 is not radially aligned while axially aligned, and the liquid delivery device 200 can be rotated until the projections 804 of the liquid delivery device 200 fits into the detents 802 of the cap device 100, thereby leaving the liquid delivery device 200 in the radial alignment position.

One or more features of the liquid delivery device 200 can be detected to determine that the liquid delivery device 200 is in the radial alignment position relative to the cap device 100. In some embodiments, as described in FIGS. 6A and 6B, the liquid delivery device 200 has one or more windows 220 formed on the reservoir 201. In an example embodiment, the liquid delivery device 200 has two windows 220 arranged opposite sides of the reservoir 201. The window 220 can longitudinally extend along the reservoir 201 has opposite axial edges 222 and 224. For example, a distal edge 222 of the window 220 (or a chamfer formed at the distal edge 222) can be used as a reference feature that the sensors in the cap device 100 should detect to verify the radial alignment of the liquid delivery device 200 relative to the cap device 100. As illustrated in FIG. 6A, when the liquid delivery device 200 is axially inserted, the distal edge 222 of the window 220 is not positioned within a field of view of the sensor 142 of the cap device 100, and thus the sensor 142 generates sensor signals indicative of misalignment between the distal edge 222 and the field of view of the sensor 142. However, as illustrated in FIG. 6B, as the liquid delivery device 200 is radially rotated and the distal edge 222 falls within the field of view of the sensor 142, the sensor signals generated from the sensor 142 changes (e.g., signal drop), which indicates that the distal edge 222 is aligned with the field of view of the sensor 142. If the liquid delivery device 200 is further rotated past the radial alignment position, the sensor signals from the sensor 142 would change back to signals identical or similar to the signals generated when the sensor 142 is not aligned with the distal edge 222 of the window 220 as illustrated in FIG. 6A.

Figure 7:
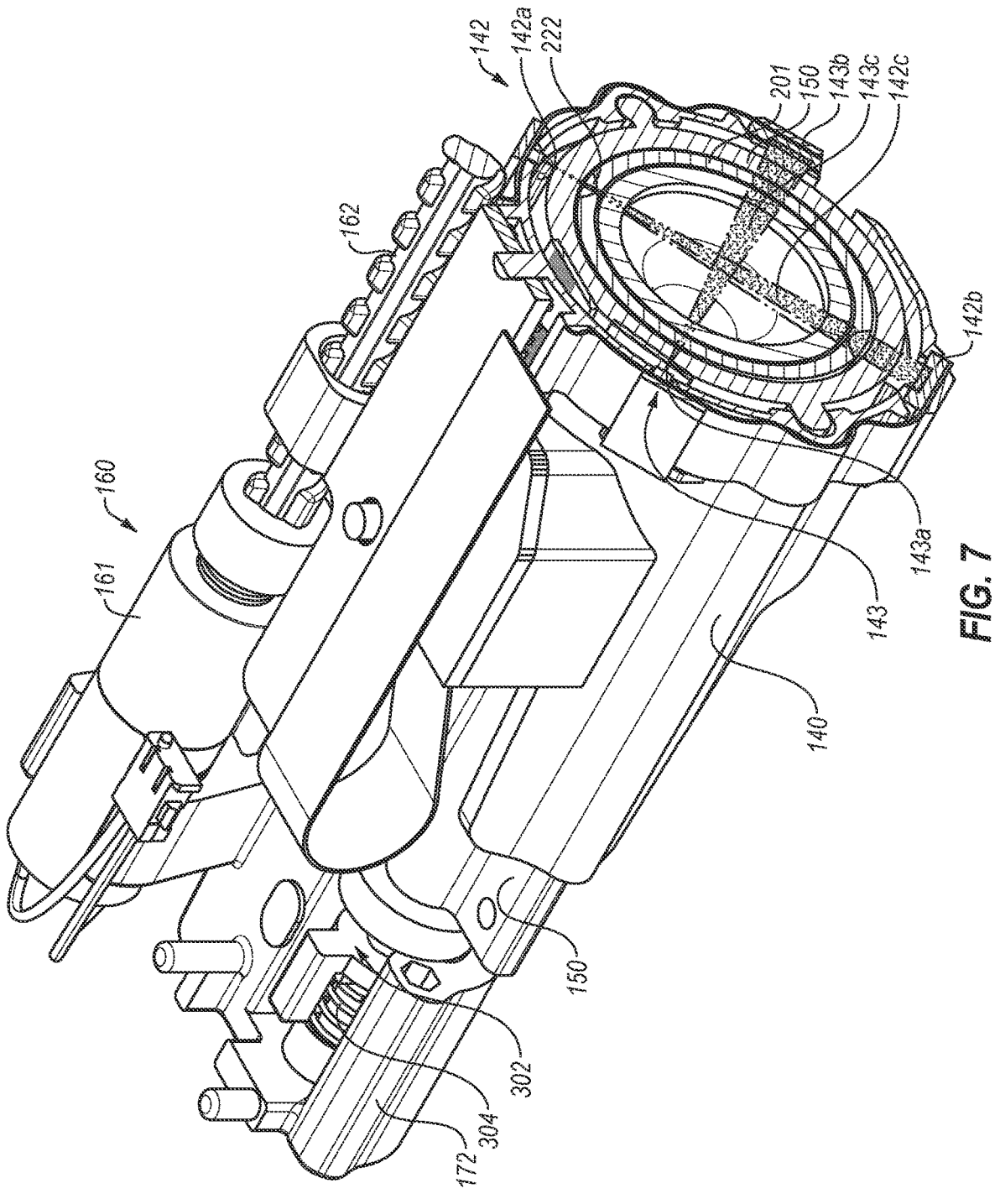
FIG. 7 is a perspective cross sectional view of parts of a cap device and a liquid delivery device, illustrating a predetermined feature of the liquid delivery device detected by a sensor of the cap device when the liquid delivery device is engaged with the cap device in a predetermined alignment position.

FIG. 7 is a cross sectional view of parts of the cap device 100 and the liquid delivery device 200 to illustrate that a predetermined feature of the liquid delivery device 200 is detected by a sensor of the cap device when the liquid delivery device 200 is engaged with the cap device 100 in the alignment position. In this illustration, the sensor 142 of the cap device 100 detects the distal edge 222 of the window 220 of the liquid delivery device 20, which represents that the liquid delivery device 200 is in radial alignment relative to the cap device 100. For example, the distal edge 222 of the window 220 formed in the reservoir 201 of the liquid delivery device 200 is aligned with the field of view 142c of the sensor 142 so that the sensor 142 generates sensor signals (e.g., signal drops) different than sensor signals that the sensor 142 generates when other features (e.g., the exterior of the reservoir 201 other than the window 220) are within the field of view 142c of the sensor 142.

Other types of the sensor 142 can be used to detect the radial alignment of the liquid delivery device. In one example embodiment, the sensor can be an infrared (IR) reflected beam sensor which can be configured to reflect an IR beam off near the surface to detect a chamfer on the distal edge 222 of the window 220 when the liquid delivery device is in the proper radial position. The sensor includes an emitter and a receiver that are arranged on the same side relative to the reservoir. The emitter transmits an IR beam which passes through the reservoir and then reflects off a mirror arranged the other side from the emitter, and the receiver receives the reflected beam that returns through the reservoir. A signal distortion due to the window can indicate the liquid delivery device is properly aligned.

In addition or alternatively, the sensor can be an IR end beam sensor. An emitter of the sensor can inject an IR beam into the distal end of the liquid delivery device, and a receiver detects the energy emitted from the chamfer of the window of the reservoir. Geometric filtering may be used with the receiver to discern the signal.

In addition or alternatively, the sensor is arranged to utilize a window recess. For example, an emitter of the sensor transmits a through-beam IR signal near the tangency of the reservoir barrel. When the liquid delivery device is in the proper radial alignment position, the window of the reservoir provides a recess with a predetermined width which can provide a discernable signal.

In addition or alternatively, the sensor is configured to scan the reservoir and/or other parts of the liquid delivery device. For example, the sensor is used to perform a half scan to detect distinct features, such as text, tick marks, window ribs, etc., that may indicate that the liquid delivery device is out of position. If the out-of-position features are detected through the scanning, the user may be requested to rotate the liquid delivery device until the liquid delivery device snaps into the detent position. Such rotation may be detected by an accelerometer or similar component in the cap device, and a half scan may be run again to confirm no out-of-position features are detected.

In addition or alternatively, the cap device includes a flexible member that can interact with the exterior surface of the reservoir of the liquid delivery device. The flexibility of the member will cause the member to change its shape depending on the part of the reservoir that the member interacts. The flexible member can be associated with a physical switch that operates to detect a different motion and/or shape of the member against the reservoir of the liquid delivery device.

In addition or alternatively, the sensor has an emitter configured to emit an IR beam at a low angle onto the reservoir or other part of the liquid delivery device. As the liquid delivery device rotates in and out of the window area, the reflection will shift as the surface of the liquid delivery device transitions from plastic to glass or vice versa. Only the beam reflected off the glass is allowed to reach a receiver of the sensor.

FIG. 8 is a cross sectional view of parts of the cap device 100 and the liquid delivery device 200 to illustrate an example radial retention structure 800 to removably retain the liquid delivery device 200 and/or generate a mechanical feedback to confirm the radial alignment of the liquid delivery device 200 relative to the cap device 100. Referring to FIGS. 3 and 8, in some embodiments, a portion of the radial retention structure 800 is provided in the sleeve 150. The radial retention structure 800 may include one or more detents 802 formed on the interior surface of the sleeve 150. In some embodiments, the sleeve 150 has one detent 802 to provide a single radial alignment for the liquid delivery device 200. In other embodiments, a plurality of detents 802 can be radially arranged on the interior surface of the sleeve 150 to provide a plurality of radial alignment positions for the liquid delivery device 200. The plurality of detents 802 may be equally spaced (i.e., at the same angular distance) along a circumference of the interior surface of the sleeve 150. In other embodiments, at least one of the plurality of detents 802 may be spaced at a different angular distance.

The radial retention structure 800 may further include one or more projections 804 that are formed on the liquid delivery device 200. The liquid delivery device 200 includes one or more projections 804 configured to fit in (e.g., snap in) the detents 802 of the cap device 100 when the liquid delivery device 200 is at least partially received in the cap device 100. The detents 802 and/or the projections 804 are arranged to engage with each other when the liquid delivery device 200 is in the alignment position (e.g., axial and/or radial alignment positions) relative to the cap device 100.

In an example embodiment, the liquid delivery device 200 includes two projections 804, each arranged on the exterior surface of the reservoir 201. For example, each of the projections 804 extends from the exterior surface of the reservoir 201 adjacent to the proximate edge 224 of the window 220 and axially aligned with the distal edge 222 of the window 220. Other locations are also possible for the projections 804 in other embodiments.

The sleeve 150 is dimensioned to axially receive the liquid delivery device 200 in any orientation. In some embodiments, the sleeve 150 is sized to accommodate at least the reservoir 201 of the liquid delivery device 200. For example, an inner diameter (ID) of the sleeve 150 is sized to be substantially identical to (with suitable clearance), or larger than, an outer diameter (OD) of the reservoir 201 that includes the projections 804. Therefore, the sleeve 150 can receive the reservoir 201 of the liquid delivery device 200 in any orientation.

The cap device 100 may include one or more ridges (or ramps) 806 formed on the interior surface of the sleeve 150. The ridges 806 provide portions raised from the inner diameter (ID) of the sleeve 150 so that the detents 802 can be formed in the ridges 806. The ridges 806 permits forming the detents 802 in the interior surface of the sleeve 150 while providing the inner diameter (ID) of the sleeve 150 sufficient to accommodate the outer diameter (OD) of the reservoir 201 of the liquid delivery device 200 that is axially inserted at orientations which arrange the projections 804 misaligned with the ridges 806.

As the projections 804 start engaging with the ridges 806 by rotating the liquid delivery device 200 relative to the cap device 100, the ridges 806 (or portions of the sleeve 150 including the ridges 806) and/or the projections 804 (or portions of the liquid delivery device 200 including the projections 804) can flex, which permits the projections 804 to slide along the ridges 806 until the projections 804 enter the detents 802.

The radial retention structure 800 may further include one or more axial stoppers 808 to prevent accidental disengagement of the projections 804 from the detents 802. The axial stoppers 808 may include flanges formed in the detents 802 and configured to engage and prevent the projections 804 from axially sliding away from the detents 802 (in an axial direction opposite to the direction in which the liquid delivery device 200 is inserted into the cap device 100) without an axial force sufficient to pull the liquid delivery device 200 out of the cap device 100 (e.g., a force exceeding a predetermined threshold force value).

The cap device 100 may further include one or more axial openings 810 extending from the detents 802 to allow axial disengagement of the projections 804 from the detents 802. The axial openings 810 are formed to extend from the detents 802 in an axial direction opposite to the direction in which the liquid delivery device 200 is inserted into the cap device 100. The axial openings 810 are configured to allow the projections 804 to slide off from the detents 802 when the liquid delivery device 200 is axially pulled from the cap device 100 with a force exceeding a predetermined threshold force value. The axial stoppers 808 may be arranged between the detents 802 and the axial openings 810 and function as bumps in the way from the detents 802 to the axial openings 810.

In some instances, the axial openings 810 can be used as entrance of the projections 804 into the detents 802 when the liquid delivery device 200 happens to be oriented (or intentionally) to align the projections 804 with the detents 802 of the sleeve 150 before being inserted into the cap device 100. In this case, an axial force that pushes the liquid delivery device 200 may overcome a resistive force from the axial stoppers 808, and the projections 804 may enter the detents 802 without rotating the liquid delivery device 200 relative to the cap device 100. The axial stoppers 808 may create a mechanical feedback (e.g., a clicking sensation) as the projections 804 are axially pushed into the detents 802.

Referring again to FIGS. 6A and 6B, the display device 121 of the cap device 100 can display various information (e.g., as symbols) to indicate different statuses of the liquid delivery device 200 and/or the cap device 100. In some embodiments, a display interface 600 of the display device 121 provides a liquid delivery device position description 602 and liquid delivery device position indicators 604 (including 604A, 604B, and 604C). As illustrated in FIG. 6B, the display interface 600 can further provide a battery status 606 and a condition 608 associated with the liquid delivery device, such as a volume of a dose delivered by the liquid delivery device, a remaining total volume of liquid within the reservoir, a remaining number of doses within the reservoir, a remaining duration until the reservoir is emptied, a time of the previous dose (e.g. a time the cap device was replaced on the liquid delivery device), an elapsed time since the last dose (e.g. an elapsed time since the cap device was replaced on the liquid delivery device), and/or other information related to the liquid delivery device.

By way of example, in a first scenario where the liquid delivery device 200 remains received in the cap device 100, the display device 121 may show the liquid delivery device condition 608 (e.g., an elapsed time since the last dose ("3 hr 10 min since last dose" in FIG. 6B)).

In a second scenario when a user removes the liquid delivery device 200 from the cap device 100, the display device 121 may change and display the liquid delivery device position description 602 to indicate the liquid delivery device has been removed (e.g., "Cap is off pen" in FIG. 6A). The display device 121 may further display first and second liquid delivery device position indicators, such as a straight arrow 604A and a curved arrow 604B, to guide the steps of engaging the liquid delivery device with the cap device in the predetermined alignment position (e.g., axial and/or radial alignment positions).

In a third scenario when a user axially inserts the liquid delivery device 200 and continues to radially rotate the liquid delivery device 200 to the predetermined alignment position (e.g., inserting and rotating the liquid delivery device within a predetermined period of time, such as 0.5 second), the display device 121 may change the display interface 600 to remove the previous description 602 (e.g., "Cap is off pen") and the previous indicators (e.g., the straight arrow 604A and the curved arrow 604B), and display a third liquid delivery device position indicator, such as a check mark 604C to represent the confirmation that the liquid delivery device 200 is in the predetermine alignment position. The display device 121 may further display the liquid delivery device condition 608.

In a fourth scenario when a user axially inserts the liquid delivery device 200 and does not rotate it to the predetermined alignment position (e.g., inserting the liquid delivery device but forgetting to rotate within a predetermined period of time, such as 0.5 second), the display device 121 may continue to display the previous description 602 (e.g., "Cap is off pen") and/or the first and second indicators, such as the straight arrow 604A and the curved arrow 604B, for a predetermined period of time since the liquid delivery device has been axially inserted (e.g., 30 seconds). After the predetermined period of time, the display device 121 may change the display interface 600 to show another description 602 (e.g., "Rotate Pen") instead of the previous description (e.g., "Cap is off pen"). The display interface 600 may be further modified to remove the first indicator (e.g., the straight arrow) 604A and continue to display the second indicator (e.g., the curved arrow) 604B, thereby informing the user that the liquid delivery device still needs to be rotated. When the user rotates the liquid delivery device to the alignment position, the description 602 (e.g., "Rotate Pen") disappears, and the second indicator (e.g., the curved arrow) 604B is replaced by the third indicator (e.g., the check mark) 604C.

The display scenarios described above may be further illustrated in FIG. 9, which is a flowchart of an example method 900 for displaying information on the cap device 100. The method 900 is described with reference also to FIGS. 6A and 6B. The method 900 may be performed at least partially by the cap device 100. The method 900 may include operation 902 of determining whether the liquid delivery device is inserted at least partially into the cap device. If the liquid delivery device is determined to not be inserted in the cap device ("No"), the method 900 moves on to operation 904. If the liquid delivery device is determined to be inserted in the cap device ("Yes"), the method 900 continues at operation 906.

The method 900 may include operation 904 of presenting first information indicating that the liquid delivery device is removed. As described in the second scenario above, the first information may include a description that indicates the liquid delivery device is removed (e.g., "Cap is off pen" in FIG. 6A). The first information may further include first and second indicators, such as the straight arrow 604A and the curved arrow 604B in FIG. 6A, to inform two steps (e.g., inserting and rotating) required to engage the liquid delivery device with the cap device in the predetermined alignment position.

The method 900 may include operation 906 of determining whether the liquid delivery device is arranged in a predetermined axial position (e.g., an axial alignment position). In some cases, determining whether the liquid delivery device is arranged in a predetermined axial position can be a determination if the cap device 100 is properly snapped onto the liquid delivery device 200 using a snap fit connection between cap device 100 and the liquid delivery device 200. If the liquid delivery device is determined to not be arranged in the predetermined axial position ("No"), the method 900 moves on to operation 908. Otherwise ("Yes"), the method 900 continues at operation 910.

The method 900 may include operation 908 of presenting second information to request axial and radial movements of the liquid delivery device relative to the cap device. The operation 908 may be performed if the liquid delivery device has not been inserted to the cap device at all, if the liquid delivery device has not been inserted enough to be in the predetermined axial position, or if the liquid delivery device is being inserted and has yet to be arranged in the predetermined axial position. The second information at the operation 908 may include a description indicating that the liquid delivery device is not aligned (e.g., "Cap is off pen" in FIG. 6A), and/or the first and second indicators, such as the straight arrow 604A and the curved arrow 604B in FIG. 6A, to show that the two steps (e.g., inserting and rotating) are still required.

The method 900 may include operation 910 of determining whether the liquid delivery device is arranged in a predetermined radial position (e.g., a radial alignment position). If the liquid delivery device is determined to not be arranged in the predetermined radial position ("No"), the method 900 moves on to operation 912. Otherwise ("Yes"), the method 900 continues at operation 914.

The method 900 may include operation 912 of presenting third information to request radial movement of the liquid delivery device relative to the cap device. The operation 912 may be performed if the liquid delivery device has been inserted to the predetermined axial position relative to the cap device but has not been rotated to the predetermined radial position. As described in the fourth scenario above, the third information may include a description 602 requesting rotation of the liquid delivery device (e.g., "Rotate Pen"), and/or a second indicator 604B (e.g., a curved arrow) notifying the user to rotate the liquid delivery device relative to the cap device.

The method 900 may include operation 914 of presenting fourth information indicating the proper alignment of the liquid delivery device. The operation 914 may be performed if the liquid delivery device has been inserted to the predetermined axial position and rotated to the predetermined radial position. As described in the third scenario above, the fourth information a third indicator 604C (e.g., a confirmation check mark) that represents the liquid delivery device 200 is confirmed to be in the predetermined alignment position.

In some embodiments, the cap device 100 operates to facilitate dosage detection at a time non-contemporaneous with dose delivery. The cap device may be configured to detect a condition of the liquid delivery device, such as a plunger position, at a time when the liquid delivery device is in an appropriate radial alignment relative to the cap device. When a user has axially inserted the liquid delivery device but failed to rotate it to a radial alignment position (e.g., forgot to do so, positioned out of alignment, etc.) (e.g., at time A), the cap device may wait until the liquid delivery device is later rotated to the radial alignment position (e.g., at time B), and operate to detect a condition associated with the liquid delivery device. In various exemplary embodiments, the cap device may output information/indicators (e.g., just before time B) to prompt the user to move the liquid delivery device to the radial alignment position. For example, the cap device may output information/indicators to prompt the user to move the liquid delivery device to the radial alignment position, even if the cap delivery device was engaged with the liquid delivery device in a misaligned position several minutes, hours, or days earlier, and/or if the display has subsequently turned off (e.g., turned off between time A and time B).

Alternatively, when the liquid delivery device is not radially aligned, the cap device may still operate to detect the condition of the liquid delivery device, and later rerun a detection process once the liquid delivery device is rotated to the radial alignment position, thereby updating the previous detection. For example, information related to a condition of the liquid delivery device determined at an earlier time (e.g., such as liquid volume within the reservoir, dosage information, volume of a previously delivered dose, other information related to the liquid delivery device and its operation), can be updated. In some example embodiments, the cap device may output further information and/or engage in subsequent operations, such as output information related to an insulin-on-board determination, recommend a correction dose, etc.

In some embodiments, the cap device may operate to record a time (also referred as, for example, a misalignment time or an axial alignment time) when the liquid device is axially engaged with the cap device, and a time (also referred to as, for example, an alignment time or a radial alignment time) when the liquid device is radially aligned relative to the cap device. The recorded times can be used to calculate and/or update with accurate determination of the condition associated with the liquid delivery device. For example, the cap device may operate to measure/calculate a dose of liquid from the liquid delivery device and log a time (e.g., the misalignment time) when the liquid delivery device is only axially inserted into the cap device and not rotated to a predetermined radial position relative to the cap device. The cap device can operate to identify a time (e.g., the alignment time) that the liquid delivery device is moved into a predetermined alignment with the cap device, and further operate to measure/calculate a dose of liquid delivered from the liquid delivery device at the earlier time, and provide the updated, accurate dose information. Such features can facilitate tracking and output of accurate information associated with the liquid delivery device over a period of time.

For example, in some cases, a user may neglect to put the cap device 100 and the liquid delivery device 200 into the predetermined radial alignment after achieving the axial alignment at time X despite radial misalignment (e.g., the presence of operation 516 in FIG. 5). If a user subsequently removes the cap device 100 from liquid delivery device 200 (e.g., for a subsequent injection of liquid) without the cap device 100 and liquid delivery device 200 previously being in the predetermined radial alignment, and then subsequently replaces the cap device 100 onto the liquid delivery device 200 in the predetermined axial and radial alignments at time Y, methods, systems, and devices provided herein can determine approximations for each of the amounts of liquid remaining in the liquid delivery device 200 at both of times X and Y. In some cases, if the cap device 100 preforms a condition detection operation (e.g., one or more of the operations 408, 410, and 412) after time X while the cap device 100 and liquid delivery device 200 are out of the predetermined radial alignment, that potentially inaccurate estimate of amount of liquid remaining can be used for time X. If no condition detection operation (e.g., the operations 408, 410, and 412) is used between times X and Y, or if no approximation can be made, methods, systems, and devices can determine the position of the plunger at time Y and infer a position of the plunger at time X based on a blood glucose response of the user at times before and after times X and Y, based on historical doses for the user at times X and times Y, based on the therapy parameters for the user, or any other information that can approximate doses. In some cases, methods, systems, and devices provided herein can query a user for a dosage amount at time X.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A cap device for a liquid delivery device, the cap device comprising:

a body defining a cavity configured to at least partially receive a liquid delivery device;

a first sensor configured to output a sensor signal indicative of a radial alignment position of the liquid delivery device relative to the body when the liquid delivery device is at least partially received within the cavity of the body; and a processor configured to detect the radial alignment position of the liquid delivery device based on the sensor signal of the first sensor; and a sensor carriage movable within the cavity between a first position and a second position while the liquid delivery device is in a fixed position relative to the cavity.

2. The cap device of claim 1, further comprising:

a second sensor configured to output a sensor signal indicative of a plunger of the liquid delivery device; and a processor configured to:

determine that the liquid delivery device is not in the radial alignment position at a first time;

determine that the liquid delivery device is in the radial alignment position at a second time later than the first time;

determine, using the second sensor, a position of the plunger at the second time; and calculate an approximated position of the plunger at the first time based at least in part on the position of the plunger at the second time.

3. The cap device of claim 2, wherein the approximated position of the plunger at the first time is based further on at least one of a blood glucose response of a user, a historical dose for the user, and a therapy parameter for the user.

4. The cap device of claim 1, wherein the first sensor is configured to output the sensor signal indicative of a radial alignment position when the first sensor is located at a predetermined axial position along the liquid delivery device.

5. The cap device of claim 1, wherein the first sensor is located on the sensor carriage.

6. The cap device of claim 1, further comprising a second sensor, the second sensor located on the sensor carriage.

7. The cap device of claim 6, wherein the second sensor is configured to output a sensor signal indicative of a plunger of the liquid delivery device while the sensor carriage moves between the first position and the second position.

8. The cap device of claim 1, wherein the first sensor includes a first optical emitter and a first optical receiver, an optical path being defined between the first optical emitter and the first optical receiver, wherein the first sensor operates to detect a physical feature by outputting a sensor signal indicative of the physical feature of the liquid delivery device, the cap device further comprising a position sensor configured to detect an axial position of the sensor carriage within the body, wherein the physical feature of the liquid delivery device includes a plunger of the liquid delivery device, and wherein the processor operates to detect the plunger of the liquid delivery device based on a variation in the sensor signal and to determine a corresponding position of the plunger based on a sensor signal output by the position sensor.

9. The cap device of claim 1, further comprising:

an axial position device configured to engage the liquid delivery device being axially inserted to the cavity of the body and generating a first mechanical feedback upon engagement of the liquid delivery device with the axial position device.

10. The cap device of claim 9, wherein the axial position device includes a sensor configured to generate a sensor signal indicative of the engagement of the liquid delivery device with the axial position device.

11. The cap device of claim 1, wherein the body is configured to axially receive at least a portion of the liquid delivery device in the cavity, the liquid delivery device being at least partially rotatable relative to the body while the at least a portion of the liquid delivery device is within the cavity.

12. The cap device of claim 1, further comprising a sleeve configured to receive at least a portion of the liquid delivery device, wherein the sensor carriage is configured to move along an outside of the sleeve.

13. A method for operating a cap device for a liquid delivery device, the method comprising:

detecting a radial position of a liquid delivery device relative to a body of a cap device while the liquid delivery device is at least partially within the cap device; and outputting information related to the radial position of the liquid delivery device, wherein detecting a radial position of a liquid delivery device comprises:

receiving, from a first sensor, a sensor signal indicative of a radial alignment position of the liquid delivery device relative to the body of the cap device, the method further comprising:

driving a sensor carriage including the first sensor to a predetermined axial location within the cap device, wherein, when the sensor carriage is arranged at the predetermined axial location, the first sensor is configured to generate the sensor signal indicative of the radial alignment position.

14. The method of claim 13, further comprising:

prior to detecting the radial position, detecting engagement of the liquid delivery device with the cap device, the liquid delivery device rotatable relative to the body of the cap device, and activating the cap device when the liquid delivery device is moved into a predetermined axial alignment position.

15. The method of claim 13, further comprising:

generating a second mechanical feedback when the radial position of the liquid delivery device is moved into the predetermined radial alignment position;

detecting a first time at which the liquid delivery device is axially engaged in a cavity of the body;

detecting a second time at which the liquid delivery device is in the predetermined radial alignment position;

detecting, using a sensor, a feature associated with the liquid delivery device; and determining a condition associated with the liquid delivery device based on the feature, the first time, and the second time.

16. The method of claim 13, further comprising:

determining that the liquid delivery device is not in radial alignment with the body of the cap device at a first time;

determining that the liquid delivery device is in radial alignment with the body of the cap device at a second time later than the first time;

determining a position of a plunger at the second time; and calculating an approximated position of the plunger at the first time based at least in part on the position of the plunger at the second time.

17. The method of claim 13, further comprising:

upon detecting the radial position of the liquid delivery device, driving a sensor carriage including a second sensor between a first position and a second position within the body of the cap device; and detecting a physical feature of the liquid delivery device while the sensor carriage moves between the first position and the second position, wherein detecting a physical feature of the liquid delivery device comprises receiving, from the second sensor, a sensor signal indicative of a sensor signal indicative of a plunger of the liquid delivery device while the sensor carriage moves between the first position and the second position.

18. A cap device for a liquid delivery device, the cap device comprising:

a body defining a cavity configured to at least partially receive a liquid delivery device;

a first sensor configured to output a sensor signal indicative of a radial alignment position of the liquid delivery device relative to the body when the liquid delivery device is at least partially received within the cavity of the body;

a second sensor configured to output a sensor signal indicative of a plunger of the liquid delivery device; and a processor configured to:

determine that the liquid delivery device is not in the radial alignment position at a first time;

determine that the liquid delivery device is in the radial alignment position at a second time later than the first time;

determine, using the second sensor, a position of the plunger at the second time; and calculate an approximated position of the plunger at the first time based at least in part on the position of the plunger at the second time.

19. The cap device of claim 18, wherein the approximated position of the plunger at the first time is based further on at least one of a blood glucose response of a user, a historical dose for the user, and a therapy parameter for the user.

\* \* \* \* \*